US011517435B2

(12) United States Patent
Chen

(10) Patent No.: US 11,517,435 B2
(45) Date of Patent: Dec. 6, 2022

(54) RING-BASED PROSTHETIC CARDIAC VALVE

(71) Applicant: Edwards Lifesciences Corporation, Irvine, CA (US)

(72) Inventor: Harvey H. Chen, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 713 days.

(21) Appl. No.: 16/392,333

(22) Filed: Apr. 23, 2019

(65) Prior Publication Data

US 2019/0336286 A1 Nov. 7, 2019

Related U.S. Application Data

(60) Provisional application No. 62/666,864, filed on May 4, 2018.

(51) Int. Cl.
*A61F 2/24* (2006.01)
*A61B 17/04* (2006.01)
*A61B 17/00* (2006.01)

(52) U.S. Cl.
CPC .......... *A61F 2/2454* (2013.01); *A61F 2/2409* (2013.01); *A61F 2/2445* (2013.01);
(Continued)

(58) Field of Classification Search
CPC .... A61F 2/2445; A61F 2/2454; A61F 2/2409; A61F 2/2463; A61F 2/2457; A61F 2/2412; A61B 2017/0464; A61B 2017/00243
See application file for complete search history.

(56) References Cited

U.S. PATENT DOCUMENTS 3,131,957 A 5/1964 Musto
3,752,516 A 8/1973 Mumma
(Continued)

FOREIGN PATENT DOCUMENTS

EP 0791330 A3 11/1997
JP 2013517110 A 5/2013
(Continued)

OTHER PUBLICATIONS

Alfieri, O. el al., "The double-orifice technique in mitral valve repair: a +A198:A225simple solution for complex problems," (2001) J. Thorne. Cardiovasc. Surg., 122(4):674-681.
(Continued)

*Primary Examiner* — Sarah A Simpson
(74) *Attorney, Agent, or Firm* — Alan T. Hale; Chang & Hale, LLP

(57) ABSTRACT

A prosthetic cardiac valve assembly and method of implanting the same is disclosed. In certain disclosed embodiments, the prosthetic valve assembly is an annuloplasty ring with an attached artificial valve. The prosthetic valve assembly can be secured to native heart tissue by suturing or other suitable method of the annuloplasty ring to the native heart tissue. The prosthetic valve leaflets of the prosthetic valve can also be anchored to the native heart tissue to prevent prolapse. In certain embodiments, the prosthetic valve leaflets are anchored to the native papillary muscles. In still other embodiments, the prosthetic valve assembly contains exactly the number of prosthetic valve leaflets as are in the native valve that the prosthetic valve assembly is configured to replace. With the prosthetic valve assembly properly positioned, it will replace the function of the native valve.

17 Claims, 16 Drawing Sheets

(52) U.S. Cl.
CPC ............... *A61B 2017/00243* (2013.01); *A61B 2017/0464* (2013.01); *A61F 2/2463* (2013.01)

(56) References Cited

U.S. PATENT DOCUMENTS

| | | |
|---|---|---|
| 4,403,797 A | 9/1983 | Ragland, Jr. |
| 4,662,376 A | 5/1987 | Belanger |
| 4,807,625 A | 2/1989 | Singleton |
| 5,144,961 A | 9/1992 | Chen et al. |
| 5,147,316 A | 9/1992 | Castillenti |
| 5,312,423 A | 5/1994 | Rosenbluth et al. |
| 5,391,176 A | 2/1995 | de la Torre |
| 5,405,352 A | 4/1995 | Weston |
| 5,454,821 A | 10/1995 | Harm et al. |
| 5,472,446 A | 12/1995 | de la Torre |
| 5,507,754 A | 4/1996 | Green et al. |
| 5,527,323 A | 6/1996 | Jervis et al. |
| 5,554,184 A | 9/1996 | Machiraju |
| 5,626,614 A | 5/1997 | Hart |
| 5,643,293 A | 7/1997 | Kogasaka |
| 5,681,331 A | 10/1997 | de la Torre et al. |
| 5,716,368 A | 2/1998 | de la Torre et al. |
| 5,727,569 A | 3/1998 | Benetti et al. |
| 5,728,109 A | 3/1998 | Schulze et al. |
| 5,746,752 A | 5/1998 | Burkhart |
| 5,769,862 A | 6/1998 | Kammerer et al. |
| 5,797,928 A | 8/1998 | Kogasaka |
| 5,824,065 A | 10/1998 | Gross |
| 5,931,868 A | 8/1999 | Gross |
| 5,957,936 A | 9/1999 | Yoon et al. |
| 5,971,447 A | 10/1999 | Steck, III |
| 6,010,531 A | 1/2000 | Donlon et al. |
| 6,074,417 A | 6/2000 | Peredo |
| 6,269,819 B1 | 8/2001 | Oz et al. |
| 6,332,893 B1 | 12/2001 | Mortier et al. |
| 6,358,277 B1 * | 3/2002 | Duran ................... A61F 2/2412 623/2.11 |
| 6,562,051 B1 | 5/2003 | Bolduc et al. |
| 6,626,930 B1 | 9/2003 | Allen et al. |
| 6,629,534 B1 | 10/2003 | St. Goar et al. |
| 6,752,810 B1 | 6/2004 | Gao et al. |
| 6,840,246 B2 | 1/2005 | Downing |
| 6,921,408 B2 | 7/2005 | Sauer |
| 6,940,246 B2 | 9/2005 | Mochizuki et al. |
| 6,978,176 B2 | 12/2005 | Lattouf |
| 6,991,635 B2 | 1/2006 | Takamoto et al. |
| 6,997,950 B2 | 2/2006 | Chawla |
| 7,112,207 B2 | 9/2006 | Allen et al. |
| 7,291,168 B2 | 11/2007 | Macoviak et al. |
| 7,294,148 B2 | 11/2007 | McCarthy |
| 7,309,086 B2 | 12/2007 | Carrier |
| 7,316,706 B2 | 1/2008 | Bloom et al. |
| 7,373,207 B2 | 5/2008 | Lattouf |
| 7,431,692 B2 | 10/2008 | Zollinger et al. |
| 7,513,908 B2 | 4/2009 | Lattouf |
| 7,534,260 B2 | 5/2009 | Lattouf |
| 7,608,091 B2 | 10/2009 | Goldfarb et al. |
| 7,618,449 B2 | 11/2009 | Tremulis et al. |
| 7,632,308 B2 | 12/2009 | Loulmet |
| 7,635,386 B1 | 12/2009 | Gammie |
| 7,666,196 B1 | 2/2010 | Miles |
| 7,744,609 B2 | 6/2010 | Allen et al. |
| 7,837,727 B2 | 11/2010 | Goetz et al. |
| 7,871,368 B2 | 1/2011 | Zollinger et al. |
| 7,871,433 B2 | 1/2011 | Lattouf |
| 7,959,650 B2 | 6/2011 | Kaiser et al. |
| 8,029,518 B2 | 10/2011 | Goldfarb et al. |
| 8,029,565 B2 | 10/2011 | Lattouf |
| 8,043,368 B2 | 10/2011 | Crabtree |
| 8,147,542 B2 | 4/2012 | Maisano et al. |
| 8,226,711 B2 | 7/2012 | Mortier et al. |
| 8,241,304 B2 | 8/2012 | Bachman |
| 8,252,050 B2 | 8/2012 | Maisano et al. |
| 8,287,591 B2 | 10/2012 | Keidar |
| 8,292,884 B2 | 10/2012 | Levine et al. |
| 8,303,622 B2 | 11/2012 | Aikhatib |
| 8,333,788 B2 | 12/2012 | Maiorino |
| 8,382,829 B1 | 2/2013 | Call et al. |
| 8,439,969 B2 | 5/2013 | Gillinov et al. |
| 8,454,656 B2 | 6/2013 | Tuval |
| 8,465,500 B2 | 6/2013 | Speziali |
| 8,475,525 B2 | 7/2013 | Maisano et al. |
| 8,500,800 B2 | 8/2013 | Maisano et al. |
| 8,608,758 B2 | 12/2013 | Singhatat et al. |
| 8,663,278 B2 | 3/2014 | Mabuchi et al. |
| 8,771,296 B2 | 7/2014 | Nobles et al. |
| 8,778,016 B2 * | 7/2014 | Janovsky ............ A61B 17/0401 623/2.11 |
| 8,828,053 B2 | 9/2014 | Sengun et al. |
| 8,852,213 B2 | 10/2014 | Gammie et al. |
| 8,888,791 B2 | 11/2014 | Jaramillo et al. |
| 8,940,008 B2 | 1/2015 | Kunis |
| 9,131,884 B2 | 9/2015 | Holmes et al. |
| 9,192,287 B2 | 11/2015 | Saadat et al. |
| 2002/0013571 A1 | 1/2002 | Goldfarb et al. |
| 2003/0023254 A1 | 1/2003 | Chiu |
| 2003/0094180 A1 | 5/2003 | Benetti |
| 2003/0105519 A1 | 6/2003 | Fasol et al. |
| 2003/0120264 A1 | 6/2003 | Lattouf |
| 2003/0120341 A1 | 6/2003 | Shennib et al. |
| 2004/0044365 A1 | 3/2004 | Bachman |
| 2004/0093023 A1 | 5/2004 | Allen et al. |
| 2004/0199183 A1 | 10/2004 | Oz et al. |
| 2005/0004667 A1 | 1/2005 | Swinford et al. |
| 2005/0019735 A1 | 1/2005 | Demas |
| 2005/0075654 A1 | 4/2005 | Kelleher |
| 2005/0075727 A1 * | 4/2005 | Wheatley ............. A61F 2/2457 623/2.17 |
| 2005/0149067 A1 | 7/2005 | Takemoto et al. |
| 2005/0149093 A1 | 7/2005 | Pokorney |
| 2005/0154402 A1 | 7/2005 | Sauer et al. |
| 2005/0216036 A1 | 9/2005 | Nakao |
| 2005/0216077 A1 | 9/2005 | Mathis et al. |
| 2005/0261710 A1 | 11/2005 | Sakamoto et al. |
| 2005/0267493 A1 | 12/2005 | Schreck et al. |
| 2006/0030866 A1 | 2/2006 | Schreck |
| 2006/0100698 A1 | 5/2006 | Lattouf |
| 2006/0111739 A1 | 5/2006 | Staufer et al. |
| 2006/0167541 A1 | 7/2006 | Lattouf |
| 2006/0190030 A1 | 8/2006 | To et al. |
| 2006/0282088 A1 | 12/2006 | Ryan |
| 2007/0001857 A1 | 1/2007 | Hartmann et al. |
| 2007/0049952 A1 | 3/2007 | Weiss |
| 2007/0055292 A1 | 3/2007 | Ortiz et al. |
| 2007/0112422 A1 | 5/2007 | Dehdashtian |
| 2007/0112425 A1 | 5/2007 | Schaller et al. |
| 2007/0118151 A1 * | 5/2007 | Davidson ............ A61B 17/0469 606/151 |
| 2007/0118154 A1 | 5/2007 | Crabtree |
| 2007/0149995 A1 | 6/2007 | Quinn et al. |
| 2007/0197858 A1 | 8/2007 | Goldfarb et al. |
| 2007/0213582 A1 | 9/2007 | Zollinger et al. |
| 2007/0270793 A1 | 11/2007 | Lattouf |
| 2008/0004597 A1 | 1/2008 | Lattouf et al. |
| 2008/0009888 A1 | 1/2008 | Ewers et al. |
| 2008/0065203 A1 | 3/2008 | Khalapyan |
| 2008/0140093 A1 | 6/2008 | Stone et al. |
| 2008/0167714 A1 | 7/2008 | St. Goar et al. |
| 2008/0188893 A1 | 8/2008 | Selvitelli et al. |
| 2008/0228223 A1 | 9/2008 | Alkhatib |
| 2008/0249504 A1 | 10/2008 | Lattouf et al. |
| 2008/0269781 A1 | 10/2008 | Funamura et al. |
| 2009/0005863 A1 | 1/2009 | Goetz et al. |
| 2009/0043153 A1 | 2/2009 | Zollinger et al. |
| 2009/0105729 A1 | 4/2009 | Zentgraf |
| 2009/0105751 A1 | 4/2009 | Zentgraf |
| 2009/0276038 A1 | 11/2009 | Tremulis et al. |
| 2010/0023056 A1 | 1/2010 | Johansson et al. |
| 2010/0023117 A1 | 1/2010 | Yoganathan et al. |
| 2010/0023118 A1 | 1/2010 | Medlock et al. |
| 2010/0042147 A1 | 2/2010 | Janovsky |
| 2010/0174297 A1 | 7/2010 | Speziali |
| 2010/0179574 A1 | 7/2010 | Longoria et al. |
| 2010/0210899 A1 | 8/2010 | Schankereli |

(56) References Cited

U.S. PATENT DOCUMENTS

| | | |
|---|---|---|
| 2010/0298930 A1 | 11/2010 | Orlov |
| 2011/0015476 A1 | 1/2011 | Franco |
| 2011/0022083 A1 | 1/2011 | DiMatteo et al. |
| 2011/0022084 A1 | 1/2011 | Sengun et al. |
| 2011/0028995 A1 | 2/2011 | Miraki et al. |
| 2011/0029071 A1 | 2/2011 | Zlotnick et al. |
| 2011/0060407 A1 | 3/2011 | Ketai et al. |
| 2011/0106106 A1 | 5/2011 | Meier et al. |
| 2011/0144743 A1 | 6/2011 | Lattouf |
| 2011/0264208 A1 | 10/2011 | Duffy et al. |
| 2011/0270278 A1 | 11/2011 | Overes et al. |
| 2011/0288637 A1 | 11/2011 | De Marchena |
| 2011/0307055 A1 | 12/2011 | Goldfarb et al. |
| 2012/0004669 A1 | 1/2012 | Overes et al. |
| 2012/0143215 A1 | 6/2012 | Corrao et al. |
| 2012/0150223 A1 | 6/2012 | Manos et al. |
| 2012/0179184 A1 | 7/2012 | Orlov |
| 2012/0184971 A1 | 7/2012 | Zentgraf et al. |
| 2012/0203072 A1 | 8/2012 | Lattouf et al. |
| 2012/0226294 A1 | 9/2012 | Tuval |
| 2012/0226349 A1 | 9/2012 | Tuval et al. |
| 2013/0018459 A1 | 1/2013 | Maisano et al. |
| 2013/0035757 A1 | 2/2013 | Zentgraf et al. |
| 2013/0079873 A1* | 3/2013 | Migliazza .......... A61B 17/0401 623/2.17 |
| 2013/0166022 A1 | 6/2013 | Conklin |
| 2013/0253641 A1 | 9/2013 | Lattouf |
| 2013/0282059 A1 | 10/2013 | Ketai et al. |
| 2013/0345749 A1 | 12/2013 | Sullivan et al. |
| 2014/0031926 A1 | 1/2014 | Kudlik et al. |
| 2014/0039607 A1 | 2/2014 | Kovach |
| 2014/0067052 A1 | 3/2014 | Chau et al. |
| 2014/0114404 A1 | 4/2014 | Gammie et al. |
| 2014/0214152 A1 | 7/2014 | Bielefeld |
| 2014/0243968 A1 | 8/2014 | Padala |
| 2014/0364938 A1 | 12/2014 | Longoria et al. |
| 2015/0032127 A1 | 1/2015 | Gammie et al. |
| 2015/0045879 A1 | 2/2015 | Longoria et al. |
| 2015/0127096 A1* | 5/2015 | Rowe .................. A61L 27/50 623/2.14 |
| 2018/0168808 A1 | 6/2018 | McCarthy |

FOREIGN PATENT DOCUMENTS

| | | |
|---|---|---|
| WO | 2004037463 A1 | 5/2004 |
| WO | 2006127509 A2 | 11/2006 |
| WO | 2007119057 A1 | 10/2007 |
| WO | 2008013869 A2 | 1/2008 |
| WO | 2007100268 A3 | 10/2008 |
| WO | 2008124110 A3 | 12/2008 |
| WO | 2008143740 A3 | 2/2009 |
| WO | 2006078694 A3 | 4/2009 |
| WO | 2009081396 A2 | 7/2009 |
| WO | 2010070649 A1 | 6/2010 |
| WO | 2010105046 A1 | 9/2010 |
| WO | 2012137208 A1 | 10/2012 |
| WO | 2013003228 A1 | 1/2013 |
| WO | 2014093861 A1 | 6/2014 |
| WO | 2015020816 A1 | 2/2015 |
| WO | 2016192481 A1 | 12/2016 |

OTHER PUBLICATIONS

Barbero-Marcial, M. et al., "Transxiphoid Approach Without Median Sternotomy for the Repair of Atrial Septal Defects," (1998) Ann. Thorne. Surg., 65(3):771-774.

Braunberger, E. et al., "Very long-term results (more than 20 years) of valve repair with Carpentier's echniques in nonheumatic mitral valve insufficiency," (2001) Circulation, I 04:1-8-1-11.

Carpentier, Alain, "Cardiac valve surgery—the 'French coffection'," The Journal of Thoracic and Cardiovascular Surgery, vol. 86, No. 3, Sep. 1983, 15 pages.

David, T. E. et al., "Mitral valve repair by replacement of chordae tendineae with polytetrafluoroethylene sutures," (1991) J. Thorne. Cardiovasc. Surg., 101 (3 ):495-50 I.

David, T. E. et al., "Replacement of chordae tendineae with Gore-Tex sutures: a ten-year experience," ( 1996) J. Heart Valve Dis., 5( 4 ):352-355.

Doty, D. B. et al., "Full-Spectrum Cardiac Surgery Through a Minimal Incision: Mini-Sternotomy (Lower Half) Technique," ( 1998) Ann. Thorne. Surg., 65(2):573-577.

Duran, C. M. G. et al., "Techniques for ensuring the correct length of new mitral chords," (2003) .I. Heart Valve Dis., 12(2):156-161.

Eishi, K. et al., "Long-term results of artificial chordae implantation in patients with mitml valve prolapse," (1997) J. Heall Valve Dis., 6(6):594-598.

Frater, R. W. M. ct al., "Chordal replacement in mitral valve repair," ( 1990) Circulation, 82(suppl. IV):IV-125-IV-130.

Frater, R. W. M., "Anatomical rules for the plastic repair of a diseased mitral valve," ( 1964) Thorax. 19:458-464.

Huber, C.H. et al., "Direct Access Valve Replacement (DAVR)—are we entering a new era in cardiac surgery?" (2006) European Journal of Cardio-thoracic Surgery, 29:380-385.

Hvass, U. et al., "Papillary Muscle Sling: A New Functional Approach to Mitral Repair in Patients With Ischemic Left Ventricular Dysfunction and Functional Mitral Regurgitation," (2003) Ann. Thorne. Surg., 75:809-811.

Kasegawa, H. ct al., "Simple method for detennining proper length of allificial chordae in mitral valve repair," ( 1994) Ann. Thorne. Surg., 57(1 ):237-239.

Kobayashi, J. et al., "Ten-year experience of chordal replacement with expanded polytetrafluoroethylene in mitral valve repair," (2000) Circulation, J 02(19 Suppl 3):1ii-30-Jii-34.

Kunzelman, K. et al., "Replacement of mitral valve posterior chordae tenclincae with expanded polytetrafluoroethylene suture: a finite element study," (1996) J. Card. Surg., 11(2):136-145.

Langer, F. et al., "RING plus STRING: Papillary muscle repositioning as an adjunctive repair technique for ischemic mitral regurgitation," (2007) J. Thorne. Cardiovasc. Surg., 133( I): 247-249.

Maisano, F. et al., "The double-orifice technique as a standardized approach to treat mitral regurgitation due to severe myxomatous disease: surgical technique," (2000) European Journal of Cardio-thorncic Surgery, 17(3):201-205.

Merendino, K. A. et al., "The open con-ection of rheumatic mitral regurgitation and/or stenosis with special reference to regurgitation treated by posteromedial annuloplasty utilizing a pump-oxygenator," (1959) Annals of Surgery, 150(1 ):5-22.

Minatoya, K. et al., "Pathologic aspects of polytetrafluoroethylene sutures in human heart," ( 1996) Ann. Thorac. Surg., 61 (3 ):883-887.

Mohty, D. ct al., "Very long-term survival and durability of mitral valve repair for mitral valve prolapse," (2001) Circulation, 104:1-1-1-7.

*Neochord, Inc. v. University of Maryland Bal Tim Ore*, Case No. JPR2016-00208, Decision on Institution of Inter Faries Review,37 CFR §42. I 08, Paper 6, Entered May 24, 2016, 28 pages.

*Neochord, Inc. v. University of Maryland Baltimore*, Case No. IPR2016-00208, Declaration of Dr. Lishan Aklog, dated Nov. 17, 2015, 91 pages.

Nigro, J. J. et al., "Neochordal repair of the posterior mitral leaflet," (2004) J. Thorne. Cardiovasc. Surg., 127(2):440-447.

Phillips, M. R. et al., "Repair of anterior leaflet mitral valve prolapse: chordal replacement versus chordal shrntening," (2000) Ann. Thorac. Surg., 69(1 ):25-29.

Russo, M. J. ct al. •Transapical Approach for Mitral Valve Repair during Insertion of a Left Ventricular Assist Device, Hindawi Publishing Corporation, The Scientific World Journal, vol. 2013, Article ID 925310, [ online], Retrieved from the internet: <URL: http://dx.doi.org/J 0.1155/2013/92531 O> Apr. 11, 2013, 4 pages.

Sarsam, M.A. I., "Simplified technique for determining the length of artificial cllordae in milral valve repair," (2002) Ann. Thorac. Surg., 73(5): 1659-1660.

Savage, E. B. et al., Use of mitral valve repair: analysis of contemporary United States experience reported to the society of thoracic surgeons national cardiac database, .. (2003) Ann. Thorne. Surg., 75:820-825.

(56) References Cited

OTHER PUBLICATIONS

Speziali, G. et al., "Coll'ection of Mitral Valve Regurgitation by Off-Pump, Transapical Placement of Artificial Chordae Tendinae, Results of the European TACT Trial," AATS 93rd Annual Meeting 2013, www.aats.org, 26 pages.

Suematsu, Y. et al., "Three-dimensional echo-guided beating heaii surgery without cardiopulmonary bypass: Atrial septal defect closure in a swine model," (2005) J. Thorne. Cardiovasc. Surg., 130: 1348-1357.

Von Oppell, U. 0. et al., "Chordal replacement for both minimally invasive and conventional mitral valve surgery using prcrncasurcd Gore-Tex loops," (2000) Ann. Thorne. Surg., 70(6):2166-2168.

Zussa, C. et al., Artificial mitral valve chordae: experimental and clinical experience; ( 1990) Ann. Thorne. Surg., 50(3):367-373.

Zussa, C. et al., "Seven-year experience with chordal replacement with expanded polytetrafluoroethylene in floppymitral valve," (1994)1. Thorac. Cardiovasc. Surg., 108(1):37-41.

Zussa, C. et al., "Surgical technique for artificial mitral chordae implantation," (1991) Journal of Cardiac Surgery, 6(4):432-438.

Zussa, C., "Artificial chordae," (1995) J. Heart Valve Dis., 4(2):S249-S256.

\* cited by examiner

RING-BASED PROSTHETIC CARDIAC VALVE

CROSS REFERENCE TO RELATED APPLICATION

This application claims the benefit to U.S. Application No. 62/666,864, filed May 4, 2018, and entitled RING-BASED PROSTHETIC CARDIAC VALVE, the disclosure of which is hereby incorporated by reference in its entirety.

BACKGROUND

Technical Field

The present disclosure generally relates to the field of prosthetic heart valves and a method for implanting prosthetic heart valves.

Description of Related Art

Biocompatible implant devices, such as heart valves, may be implanted in patients to treat various conditions. Replacement of implanted prosthetic heart valves can be associated with certain complications and/or issues.

SUMMARY

Certain prosthetic cardiac valve assemblies and method of implanting the same are disclosed. Prosthetic valves in accordance with the present disclosure may comprise, for example, replacement mitral or tricuspid valve devices and/or assemblies. In some implementations, prosthetic valves and valve assemblies disclosed herein provide ring-based valves, such as ring-based mitral or tricuspid valves. In some implementations, prosthetic valve designs in accordance with the present disclosure comprise an annuloplasty ring mounted with tissue in a geometry that mimics the native mitral valve leaflets. Artificial chordae tendineae may be attached or attachable to the leaflet and/or the papillary muscles using any suitable or desirable technique or technology.

In one exemplary embodiment, a prosthetic cardiac valve assembly includes a ring, valve leaflets, and anchor lines. The valve leaflets are attached to the ring. The anchor lines are attached to the valve leaflets. The anchor lines can be attached to native tissue, such as papillary muscles. The prosthetic valve assembly can replace and function in substantially the same manner as the native valve.

In certain disclosed embodiments, the prosthetic valve assembly comprises an annuloplasty ring with an attached artificial valve. The prosthetic valve assembly can be secured to native heart tissue by suturing, or other suitable method, of the annuloplasty ring to the native heart tissue. The prosthetic valve leaflets of the prosthetic valve can also be anchored to the native heart tissue to prevent prolapse. In certain embodiments, the prosthetic valve leaflets are anchored to the native papillary muscles. The prosthetic valve assembly, as properly positioned and/or configured, can, in some embodiment, replace the function of the native valve. In certain embodiments, the native heart valve structure, including native chordae tendineae, is at least partially removed before the replacement prosthetic valve assembly is secured and/or the prosthetic valve leaflets are anchored.

In some embodiments, the native valve structures need not be removed. For example, where the prosthetic valve assembly is used to replace a tricuspid or mitral valve, the prosthetic valve assembly can be inserted above or below an annulus of the native valve. When positioned below the annulus of the native valve, the assembly may be sized to press into the native tissue such that the annulus itself can at least partially restrict the assembly from moving in an upward direction towards the atrium. The prosthetic valve assembly can be secured to the native valve annulus or surrounding tissue via suturing or other suitable method. In some configurations, the prosthetic valve assembly can be positioned so that the leaflets of the native valve are held in the open position.

In certain embodiments, the prosthetic valve assembly can be secured to native heart tissue by suturing or by prongs or other attachment mechanisms on an outer surface of the prosthetic valve assembly. Alternatively or additionally, a tether or other anchoring member may be attached to the prosthetic valve assembly at one end and secured to a portion of the heart at another end in order to prevent movement of the prosthetic valve assembly after implantation.

In certain embodiments, prosthetic valve leaflets are anchored to native heart tissue using attachment techniques that are described in U.S. Patent Application Publication No. 2014/0114404, which is hereby incorporated by reference. The incorporated reference is related to the anchoring of native valve leaflets to native heart tissue. The present disclosure describes the inventive application of certain anchoring techniques, such as those disclosed in the reference incorporated above, to prosthetic valve leaflets after implantation of a prosthetic valve.

In some embodiments, the prosthetic valve assembly contains exactly the number of prosthetic valve leaflets as are in the native valve that the prosthetic valve assembly is configured to replace. Thus, certain replacement prosthetic mitral valve assemblies can have two leaflets, and certain replacement prosthetic tricuspid valve assemblies can have three leaflets.

In certain embodiments, a method of implanting the prosthetic heart valve assembly follows the following sequence: the native heart valve is first removed, and then the prosthetic valve assembly is secured to native heart tissue in a first surgical procedure. The prosthetic valve leaflets are then subsequently anchored to native heart tissue either as a part of the surgical procedure or in a separate transcatheter or transapical procedure.

These features and others of the described embodiments will be more readily apparent from the following detailed description, which proceeds with reference to the accompanying drawings.

DETAILED DESCRIPTION OF CERTAIN EMBODIMENTS

Figure 1:
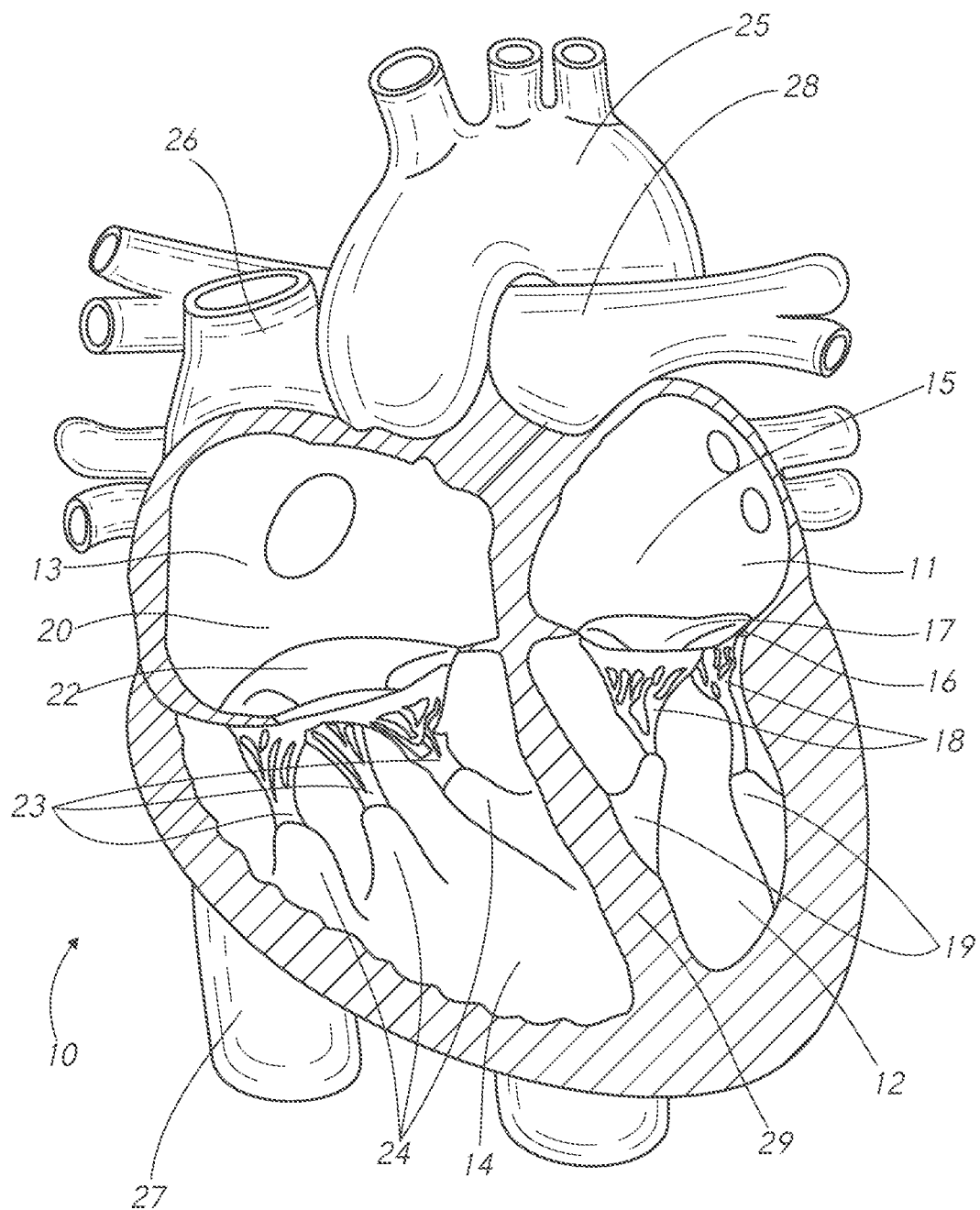
FIG. 1 is a cross-sectional view of a heart.

As used herein, the singular forms "a," "an," and "the" refer to one or more than one, unless the context clearly dictates otherwise.

As used herein, the term "includes" means "comprises." For example, a device that includes or comprises A and B contains A and B but can optionally contain C or other components other than A and B. A device that includes or comprises A or B can contain A or B, or A and B, and optionally one or more other components such as C.

Prosthetic cardiac valves have been used for many years to treat cardiac valvular disorders. The native heart valves (such as the aortic, pulmonary, tricuspid, and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise or death. Treatment for such disorders can involve the surgical repair or replacement of the valve during open heart surgery, but such surgeries are prone to many complications. More recently a transvascular technique has been developed for introducing and implanting a prosthetic heart valve using a flexible catheter in a manner that is less invasive than open heart surgery.

According to some transvascular techniques, a prosthetic valve can be mounted in a crimped state on the end portion of a flexible catheter and advanced through a blood vessel of the patient until the valve reaches the implantation site. The valve at the catheter tip is then expanded to its functional size at the site of the defective native valve such as by inflating a balloon on which the valve is mounted.

Other techniques for implanting a prosthetic aortic valve can involve a transapical procedure, where a small incision is made in the chest wall of a patient and the catheter is advanced through the apex (e.g., bottom tip) of the heart. Certain transapical techniques are disclosed in U.S. Patent Application Publication No. 2007/0112422 A1, which is hereby incorporated by reference Like the transvascular approach, the transapical approach can include a balloon catheter having a steering mechanism for delivering a balloon-expandable prosthetic heart valve through an introducer to the aortic annulus. The balloon catheter includes a deflecting segment just proximal to the distal balloon to facilitate positioning of the prosthetic heart valve in the proper orientation within the aortic annulus.

The above-described techniques and others can provide numerous options for high-risk patients with aortic valve stenosis to avoid the consequences of open heart surgery and cardiopulmonary bypass. While procedures for the aortic valve are well-developed, such procedures are not necessarily applicable to the mitral valve or tricuspid valve.

Mitral valve repair can benefit from relatively high success rates, and clinical improvements noted after repair. However, a significant percentage (e.g., about 33%) of patients still receive open-heart surgical mitral valve replacements due to calcium, stenosis, or anatomical limitations. There are a number of technologies aimed at making mitral repair a less invasive procedure. These technologies range from iterations of the Alfieri stitch procedure to coronary sinus-based modifications of mitral anatomy to subvalvular placations or ventricular remodeling devices, which would incidentally correct mitral regurgitation.

Both mitral valve replacement and tricuspid valve replacement, despite these new procedures, can be considered relatively challenging and/or underutilized due at least in part to the valves' relatively complex anatomical structures (e.g., chordae tendineae and papillary muscles) and location in the heart. Mimicking native heart valve functionality for these valves in particular can be a difficult task.

FIG. 1 is a cross-sectional view of a heart 10 including a native mitral valve 15 and a native tricuspid valve 20. The chordae tendineae 18, 23 and papillary muscles 19, 24 of the respective native valves are also shown. For purposes of background, the four-chambered heart is explained further. On the left side of the heart, the native mitral valve 15 is generally located between the left atrium 11 and left ventricle 12. The mitral valve 15 generally comprises two native leaflets 17, an anterior leaflet and a posterior leaflet. The mitral valve leaflets 17 are attached to a mitral valve annulus 16, which is defined as the portion of tissue surrounding the mitral valve orifice. The left atrium 11 receives oxygenated blood from the pulmonary veins. The oxygenated blood that is collected in the left atrium 11 enters the left ventricle 12 through the mitral valve 15.

Contraction of the left ventricle 12 forces blood through the left ventricular outflow tract and into the aorta 25. The aortic valve (not shown) is located between the left ventricle 11 and the aorta 25 to ensure that blood flows in only one direction (e.g., from the left ventricle to the aorta). As used herein, the left ventricular outflow tract (LVOT) is intended to generally include the portion of the heart through which blood is channeled from the left ventricle to the aorta.

On the right side of the heart, the native tricuspid valve 20 is located between the right atrium 13 and the right ventricle 14. The right atrium 13 receives blood from the superior vena cava 26 and the inferior vena cava 27. The superior vena cava 26 returns de-oxygenated blood from the upper part of the body and the inferior vena cava 27 returns de-oxygenated blood from the lower part of the body. The right atrium 13 also receives blood from the heart muscle itself via the coronary sinus. The blood in the right atrium 13 enters the right ventricle 14 through the tricuspid valve 20. Contraction of the right ventricle 14 forces blood through the right ventricle outflow tract and into the pulmonary arteries. The pulmonic valve (not shown) is located between the right ventricle 14 and the pulmonary trunk 28 for ensuring that blood flows in only one direction from the right ventricle 14 to the pulmonary trunk 28.

The left and right sides of the heart are separated by a wall generally referred to as the septum 29. The portion of the septum that separates the two upper chambers (the right and left atria) of the heart is termed the atrial (or interatrial) septum while the portion of the septum that lies between the two lower chambers (the right and left ventricles) of the heart is called the ventricular (or interventricular) septum. A healthy heart has a generally conical shape that tapers from a base to an apex 110.

Figure 2:
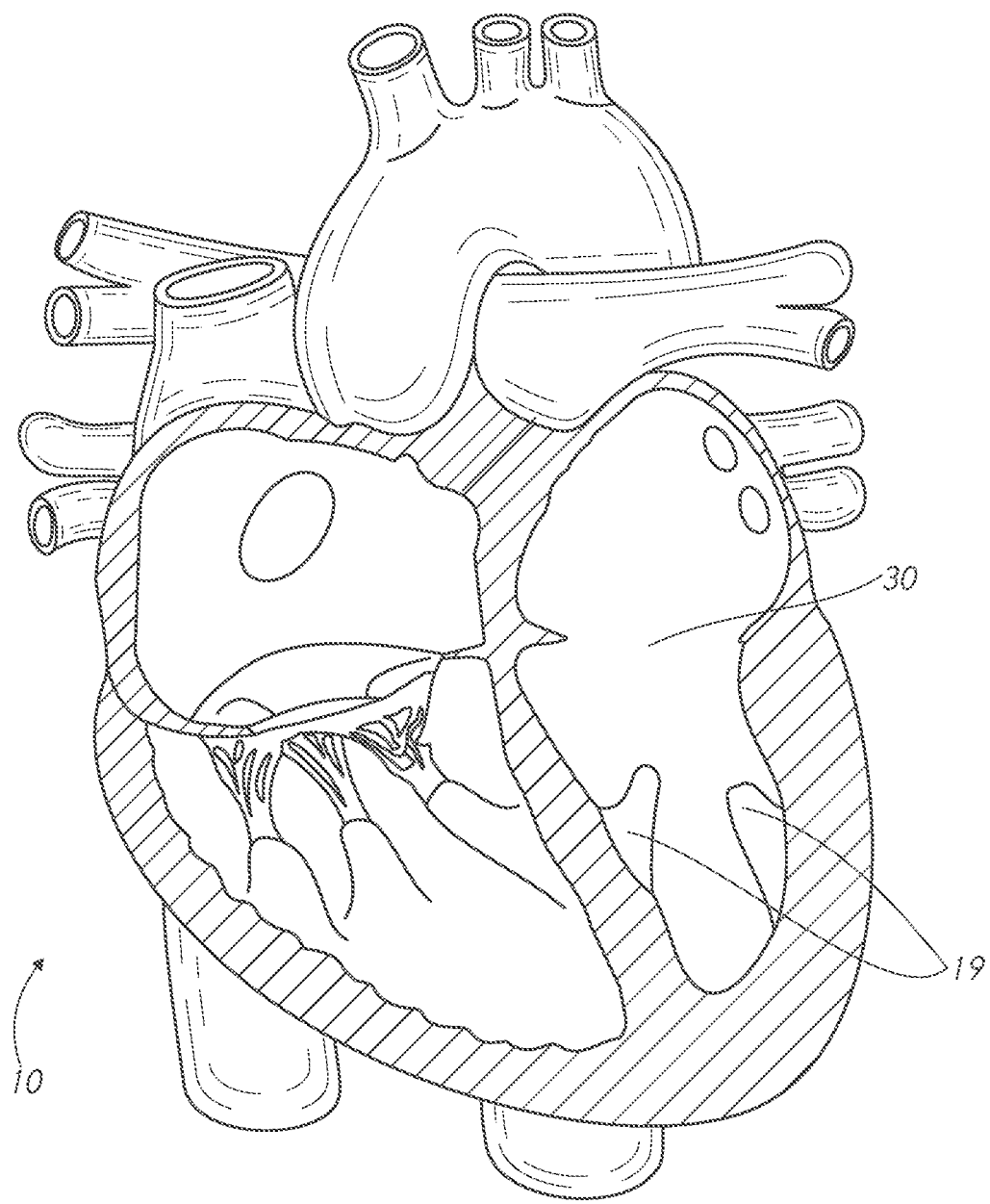
FIG. 2 is cross-sectional view of a heart with the mitral valve removed in accordance with one or more embodiments.

FIGS. 2-5 illustrate stages of an embodiment of a method for replacing a native mitral valve with a prosthetic valve assembly and one or more embodiments of a prosthetic valve assembly. In some implementations, a native mitral valve 15 (see FIG. 1) can be removed, for example, surgically removed. FIG. 2 shows the mitral valve gap 30 left behind after removal. In some implementations, the native mitral valve 15 and the attached chordae tendineae 18 are removed. The papillary muscles 19 of the left ventricle 12 may advantageously remain.

Figure 3:
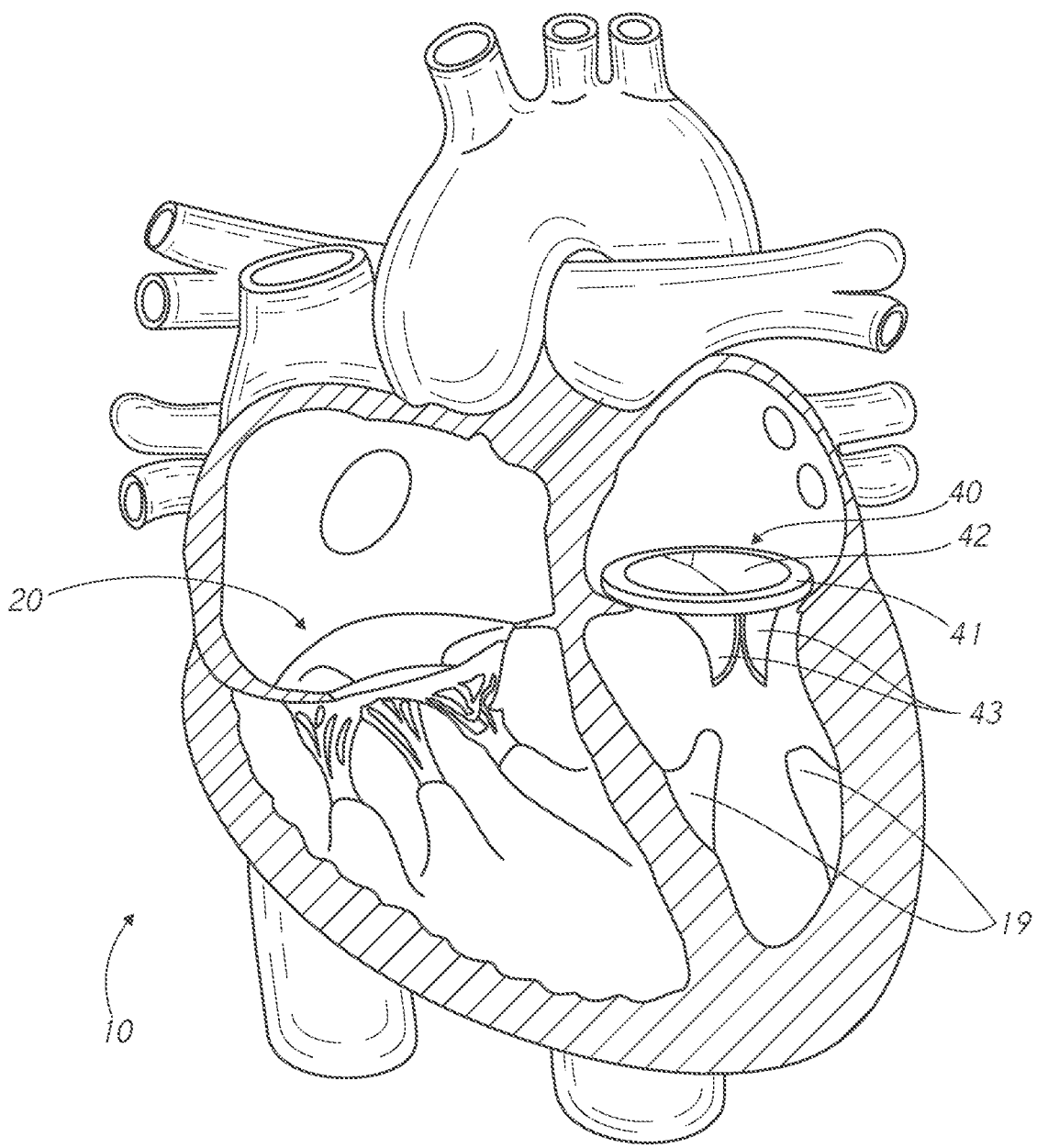
FIG. 3 is a cross-sectional view of a heart with a prosthetic valve assembly implanted in place of the native mitral valve in accordance with one or more embodiments.
Figure 4:
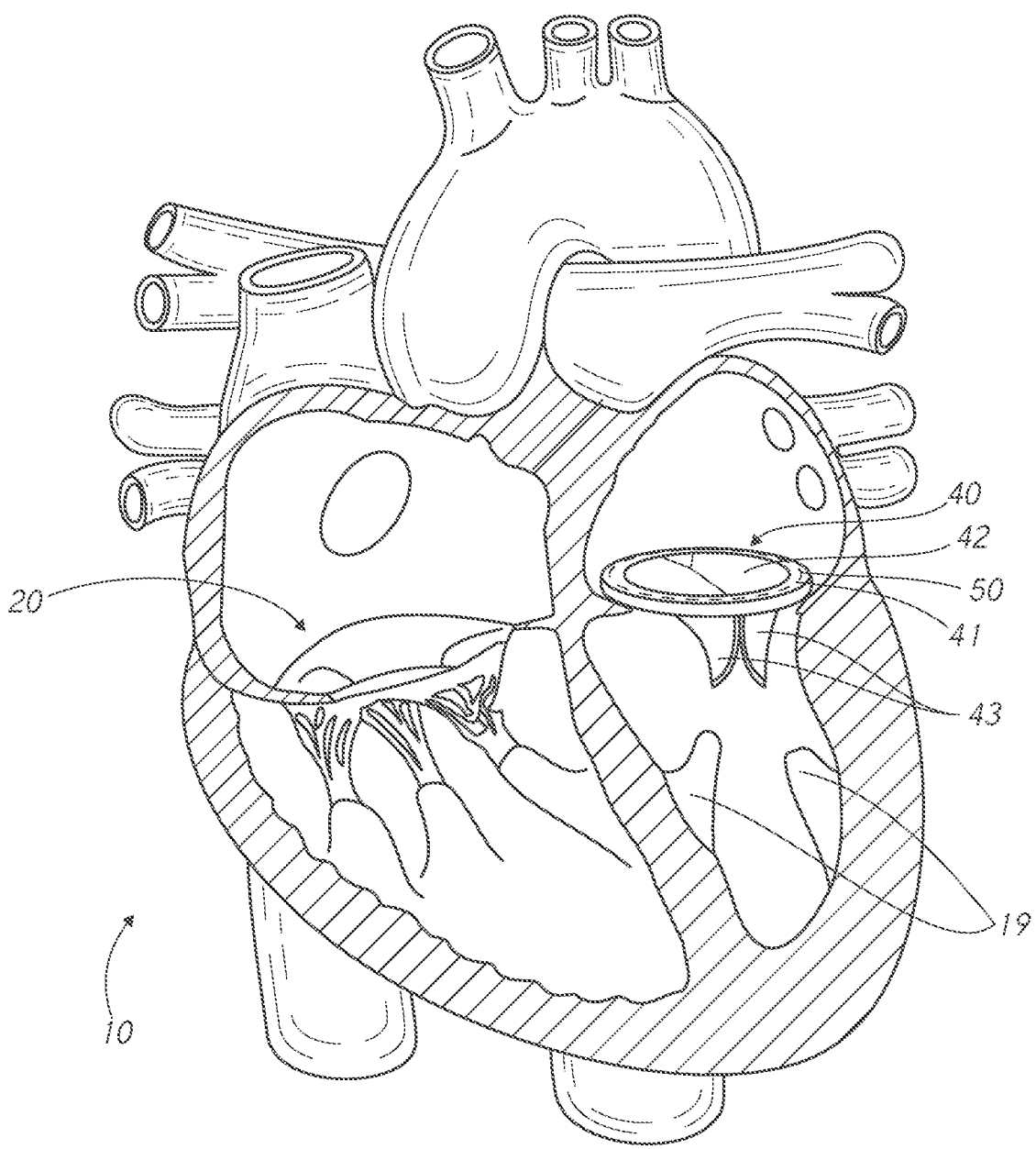
FIG. 4 is a cross-sectional view of a heart with a prosthetic valve assembly implanted in place of the native mitral valve in accordance with one or more embodiments, wherein the prosthetic valve assembly is sutured to the native heart tissue.

In certain embodiments, a prosthetic valve assembly is then surgically implanted in place of the mitral valve gap 30. A particular embodiment of a prosthetic valve assembly 40 is shown in FIG. 3. The prosthetic valve assembly 40 may comprise an annuloplasty ring 41 attached to a prosthetic valve 42 having one or more prosthetic valve leaflets 43. In certain embodiments, the prosthetic valve assembly 40 includes a prosthetic valve 42 with two prosthetic leaflets 43, thus matching the number of the native leaflets in the native mitral valve 15 it replaces. In some embodiments, the size, positioning, shape, and/or other physical characteristics of the prosthetic valve leaflets substantially match or approximate the corresponding physical properties of the removed, native heart valve leaflets. In some implementations, certain imaging techniques can be used to measure/determine the shape and/or sizes of the annulus and/or leaflets. The size and/or shape of the prosthetic valve assembly 40 and/or one or more of its components may be selected based at least in part on the measured values. The placement of the prosthetic valve assembly 40 can be above or below the dividing wall between the left atrium 11 and the left ventricle 12, or anywhere where the prosthetic valve assembly will appropriately allow flow of blood from the left atrium 11 and into the left ventricle 12 without substantial backflow.

In certain embodiments in which the prosthetic valve assembly 40 includes an annuloplasty ring 41 with a prosthetic artificial valve 42, the leaflets 43 of the attached prosthetic valve 42 may be configured to collapse into the ring's 41 physical envelope, and/or the annuloplasty ring 41 can be sized such that the prosthetic valve assembly 40 may be implanted in the heart via a minimally invasive surgical procedure. In some embodiments, the annuloplasty ring 41 can have an orifice area of from about 2 cm$^2$ to about 8.5 cm$^2$, of from about 2.3 cm$^2$ to about 8 cm$^2$, of from about 2.7 cm$^2$ to about 7.4 cm$^2$, of from about 3.25 cm$^2$ to about 6.5 cm$^2$, or of from about 2.3 cm$^2$ to about 4.8 cm$^2$. In some embodiments, the annuloplasty ring 41 can have an external, major axis or commissure-commissure (C-C) diameter of from about 25 mm to about 50 mm, of from about 28 mm to about 46 mm, of from about 30 mm to about 43 mm, of from about 31.2 mm to about 41.2 mm, or of from about 28.2 mm to about 37.8 mm. In some embodiments, the annuloplasty ring 41 can have an external, minor axis or anterior-posterior (A-P) diameter of from about 10 mm to about 30 mm, of from about 14.7 mm to about 26.1 mm, of about from 18 mm to about 23.7 mm, of from about 19 mm to about 22.4 mm, or of from about 12.7 mm to about 18.5 mm. These dimensions can also be used for sizing embodiments of prosthetic valve assemblies for replacing other cardiac valves, as well, including the tricuspid valve, for example. Embodiments of prosthetic valve assemblies for replacing cardiac valves in accordance with the present disclosure may include annuloplasty rings with one or more of the dimensions listed below in Table 1, wherein each row represents the dimensions of a single ring, but any ranges, subranges, or combinations of dimensions, ranges, and subranges may also be used. Each of FIGS. 11A-11C refer to a different configuration of annuloplasty ring.

TABLE 1

Figure 11A:
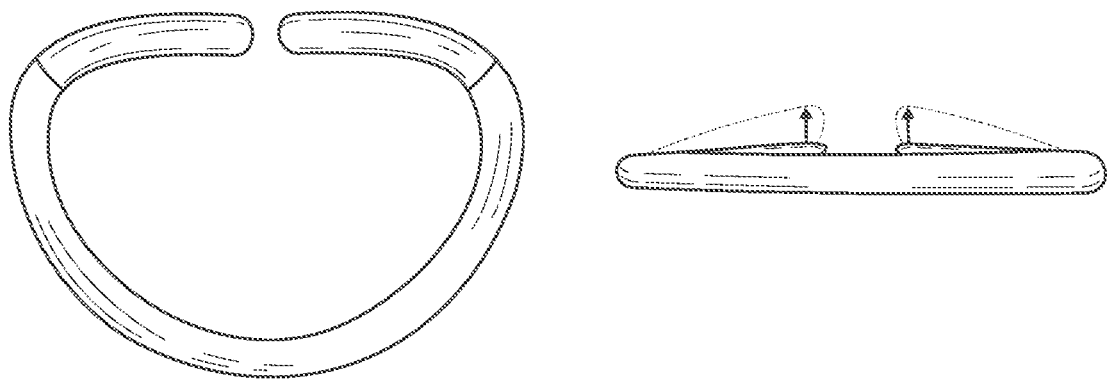
FIGS. 11A-11C are perspective views of different configurations of annuloplasty rings in accordance with one or more embodiments.
Figure 11B:
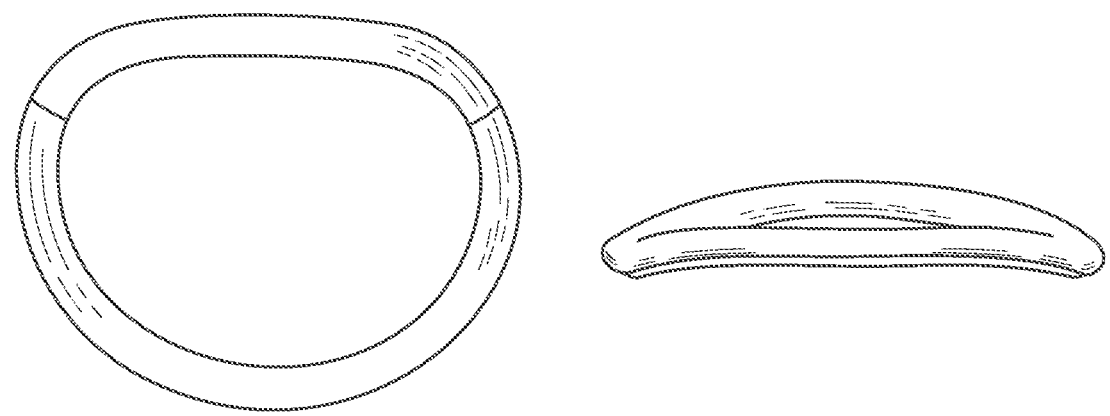
Figure 11C:
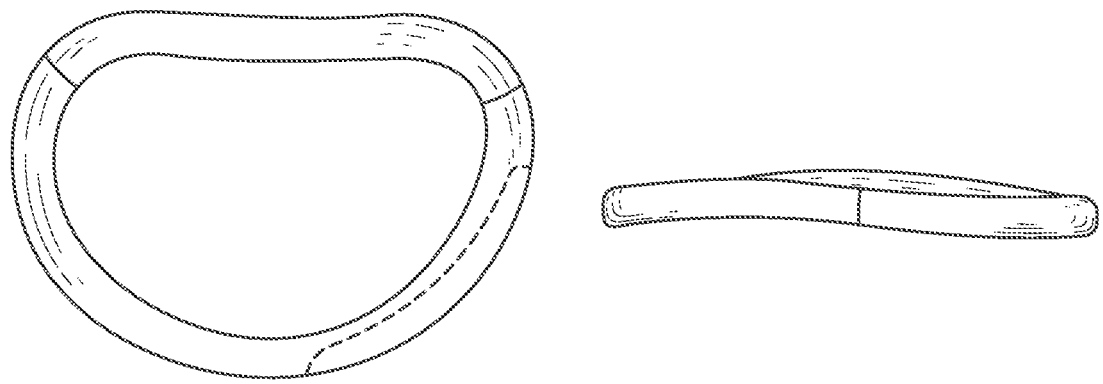

| Orifice Area (cm$^2$) | C-C Diameter (mm) | | A-P Diameter (mm) |
|---|---|---|---|
| | External | Internal | External |
| Reference FIG. 11A | | | |
| 2.88 | 31.2 | 24.3 | 14.7 |
| 3.39 | 33.2 | 26.3 | 16 |
| 3.95 | 35.2 | 28.3 | 17.3 |
| 4.55 | 37.2 | 30.3 | 18.6 |
| 5.19 | 39.2 | 32.3 | 20.9 |
| 5.86 | 41.2 | 34.3 | 21.1 |
| 6.59 | 43.4 | 36.4 | 22.4 |
| 7.36 | 45.4 | 37.5 | 23.7 |
| Reference FIG. 11B | | | |
| 2.74 | 28.7 | 22.9 | 15.2 |
| 3.25 | 30.7 | 24.9 | 16.4 |
| 3.8 | 32.9 | 26.9 | 18 |
| 4.4 | 34.9 | 28.9 | 19.2 |
| 5.04 | 37.1 | 30.9 | 20.7 |
| 5.72 | 39.1 | 32.9 | 22 |
| 6.45 | 41.2 | 34.8 | 23.3 |
| 7.22 | 43.2 | 36.8 | 24.8 |
| 8.04 | 45.3 | 38.7 | 26.11 |
| Reference FIG. 11C | | | |
| 2.28 | 28.2 | 21.8 | 12.7 |
| 2.7 | 30.1 | 23.7 | 14.9 |
| 3.17 | 32.1 | 25.7 | 15 |
| 3.67 | 34 | 27.6 | 16.2 |
| 4.21 | 35.9 | 29.5 | 17.3 |
| 4.77 | 37.8 | 31.4 | 18.5 |

The prosthetic valve portion 42 can have a leafed-valve configuration, such as a tricuspid valve configuration or the bicuspid valve configuration shown in the illustrated embodiment. The valve portion 42 can be formed from one or more pieces of flexible, pliant material connected to each other at one or more seams (also referred to as commissures or commissure tabs) to form collapsible prosthetic valve leaflets 43 and a base, or upper end, portion that connects to an annuloplasty ring. The valve portion 42 can be connected to the annuloplasty ring 41 at the seams using, for example, sutures and/or other suitable connection techniques known in the art. Alternatively, the valve portion 42 can be a mechanical type valve, rather than a leafed type valve.

The valve portion 42 can be made at least in part from biological matter, such as natural tissue, pericardial tissue (e.g., bovine, porcine, or equine pericardium), a harvested natural valve, and/or other biological tissue. Alternatively, the valve can be made from biocompatible synthetic materials (e.g., biocompatible polymers). The valve can be shaped to fit the contours of the annuloplasty ring so as to match the annuloplasty ring in diameter. Blood flow through the valve proceeds in a direction from the annuloplasty ring in the atrium, where the prosthetic valve leaflets attach, to the opposite end of the prosthetic valve leaflets in the ventricle.

A prosthetic valve assembly can be at least partially secured in some manner to the native heart tissue. In the embodiment shown in FIG. 4, the annuloplasty ring 41 of the prosthetic valve assembly 40 is sutured 50 or otherwise secured or connected to the heart tissue, such as to a portion of the annulus or dividing wall between the left atrium 11 and left ventricle 12, such that blood flows through the prosthetic valve 42 from the left atrium 11 into the left ventricle 12, but not backward to a substantial degree when the heart is functioning. In the embodiment shown, the annuloplasty ring 41 of the prosthetic valve assembly 40 is placed above and resting on the divide between left atrium 11 and left ventricle 12. In some embodiments, the prosthetic valve assembly 40 can be secured to native heart tissue other than the dividing wall between the atria and ventricles and/or can be secured via different means (e.g., hooks, pledgets, pressure/friction fitting, metal, plastic, composite or other clips, metal mesh, etc.) to the same or different structures on the prosthetic valve assembly 40 than the annuloplasty ring (e.g., the prosthetic valve or prosthetic valve leaflets). For a pressure fit, the outward radial pressure of the prosthetic valve assembly 40 against the surrounding tissue can assist at least in part in retaining the valve assembly in place.

In still further embodiments (not pictured), at least a portion of the native heart valve can remain in the heart, with the prosthetic valve assembly 40 placed to fit at least partially within or inside the native heart valve. In such embodiments, the prosthetic valve assembly 40 is placed and oriented such that blood can flow through the prosthetic valve and through the remaining native valve from the left atrium 11 to the left ventricle 12, but not back to a substantial degree while the heart is functioning. The prosthetic valve assembly can be secured to the native tissue of the heart by a pressure fit within the native valve annulus or other native heart tissue, and/or by other means of attachment members (e.g., suturing, hooks, pledgets, etc.). In such embodiments, the replacement procedure may be accomplished by implanting the prosthetic valve assembly directly over the native leaflets, which may be at least partially calcified. In this manner, the native leaflets can assist in securing the prosthetic valve assembly in place.

Figure 5:
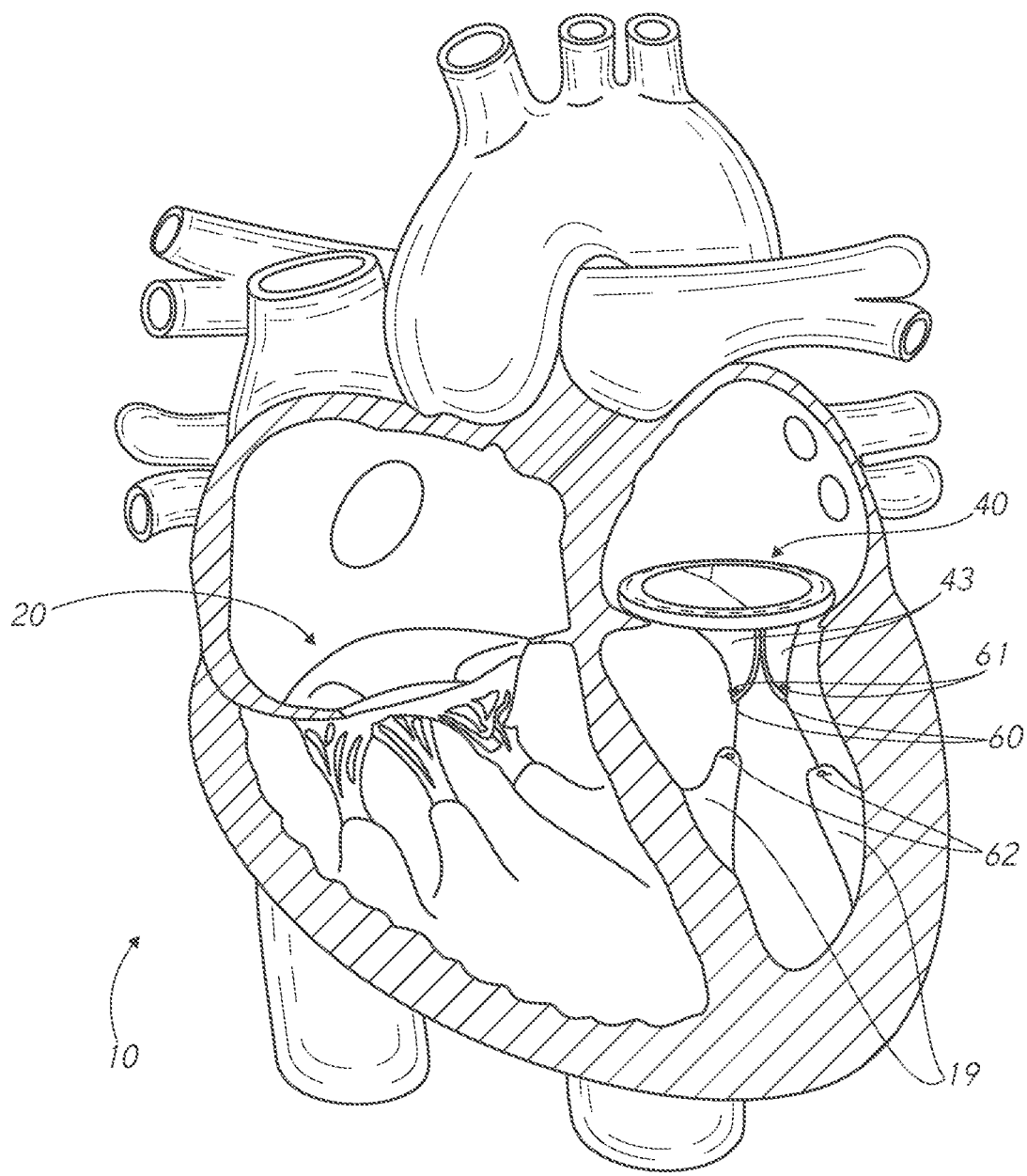
FIG. 5 is a cross-sectional view of a heart with an embodiment of a prosthetic valve assembly implanted in place of a native mitral valve, wherein the leaflets of the prosthetic valve assembly are coupled to the native papillary muscles of the left ventricle by tensioning members to simulate chordae tendineae in accordance with one or more embodiments.

In certain embodiments, the prosthetic valve leaflets 43 are at least partially anchored to native heart tissue. As shown in FIG. 5, prosthetic valve leaflets 43 can be at least partially anchored to native papillary muscles 19. In certain embodiments, the prosthetic valve assembly 40 has the same number of prosthetic leaflets as the number of leaflets in the native valve that the prosthetic valve assembly replaces or supplements. In certain embodiments, this allows the prosthetic valve assembly to advantageously sufficiently accurately mimic the native valve geometry and/or attachment and so better prevent prolapse of the prosthetic leaflets. FIG. 5 shows one such embodiment wherein the prosthetic valve assembly 40 mimics the structure of native mitral valve 15, having two leaflets 43. Each prosthetic leaflet 43 can accordingly be anchored to an existing, native papillary muscle 19. In the particular embodiment shown in FIG. 5, prosthetic leaflets 43 are tethered or otherwise physically coupled to native papillary muscles 19 via tethers 60, prosthetic valve leaflet anchors 61, and/or papillary muscle anchors 62, though other methods can also be used to anchor the prosthetic leaflets to the native tissue of the heart. In some embodiments, the prosthetic valve leaflets 43 may be anchored to native heart tissue anywhere in or through the left ventricle 12 and/or surrounding tissue. Further, in some embodiments, multiple tethers can be used to anchor a single leaflet.

In some embodiments, the prosthetic valve leaflets 43 are configured to function normally (e.g., not prolapse or not prolapse significantly) for a period of time after surgical implantation of the prosthetic valve, but before attachment of replacement chordae 60 to the leaflets and heart tissue. For example, the chordae 60 can be attached to the leaflets 43 of the prosthetic valve, for example, from about zero to about seven days after implantation of prosthetic valve assembly 40, from about one to about four weeks after implantation of prosthetic valve assembly 40, from about one to about six months after implantation of the prosthetic heart valve assembly, or within any sub-range within these ranges. That is, the valve leaflets can be configured to function normally in the relatively short term without attachment to heart tissue by replacement chordae 60. Once attached, replacement chordae can provide reinforcement for the prosthetic valve leaflets 43 to advantageously improve the functionality of the prosthetic valve. For example, the attachment of one or more of the replacement chordae 60 may facilitate functionality of the prosthetic valve with substantially no prolapse over a relatively long term after attachment (e.g., longer than one year or many years).

The tethers 60 may serve as a form of prosthetic chordae tendineae. The tethers 60 can one or more functions (e.g., de-stressing the leaflets by preventing prolapse).

In some embodiments, a prosthetic valve assembly in accordance with the present disclosure may include one or more pre-attached leaflet anchors. Such prosthetic valve assembl(ies) may be used to replace at least a portion of a cardiac valve. For example, the anchors may be attached to prosthetic valve leaflets of a prosthetic valve assembly before the prosthetic valve assembly enters and/or is implanted in the heart. The modified prosthetic valve assembly may then be inserted into the heart and secured to native heart tissue. The pre-attached anchors may then be coupled to native heart tissue to secure the prosthetic heart valve leaflets.

Prosthetic valve implantation methods in accordance with the present disclosure may involve at least partially building the replacement valve in situ. In some implementations, the implant ring and leaflets are implanted during an open-chest operation, wherein the heart is stopped. One or chordae may also be attached at that time. The bulk or remainder of the artificial chordae may be implanted in a subsequent operation or procedure during which the heart is pumping, such as through a trans-catheter procedure. In some implementations, the ring 40 may be placed in the atrium, but suturing may be performed from within the ventricle, such as in connection with a subsequent operation or procedure (e.g., percutaneous/trans-catheter operation).

Figure 6:
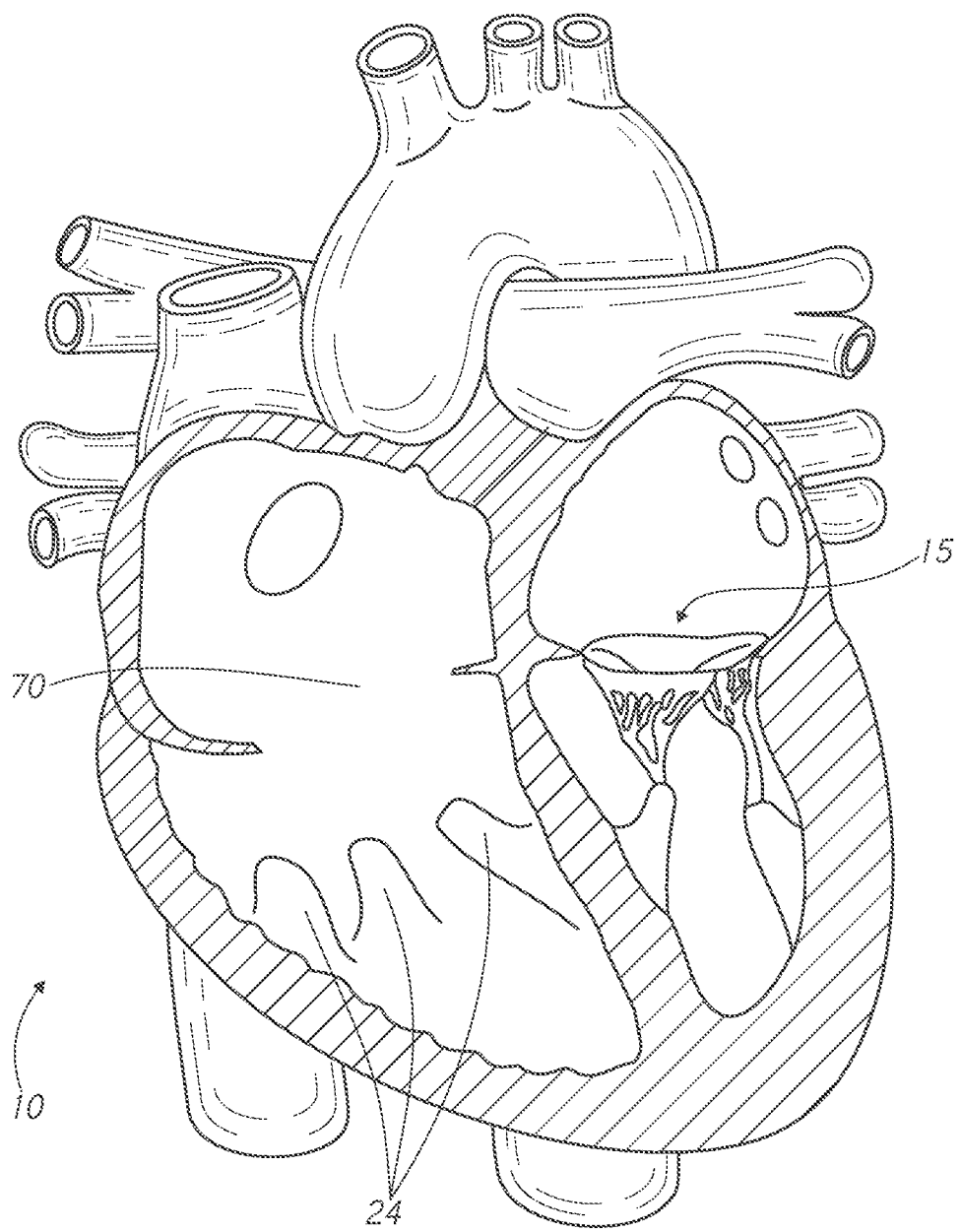
FIG. 6 is a cross-sectional view of a heart with the tricuspid valve removed in accordance with one or more embodiments.

FIGS. 6-9 illustrate various stages of one or more embodiments of a method for at least partially replacing a native tricuspid valve with a prosthetic valve assembly, and one or more embodiments of such prosthetic valve assembly. In some embodiments, the native tricuspid valve 20 may be at least partially removed. FIG. 6 shows a tricuspid valve gap 70 left behind after removal of the native mitral valve 20. The attached chordae tendineae 23 (see, e.g., FIG. 1) may also be removed. One or more of the papillary muscles 24 of the right ventricle 14 may remain, at least in part, after removal of the native tricuspid valve.

Figure 7:
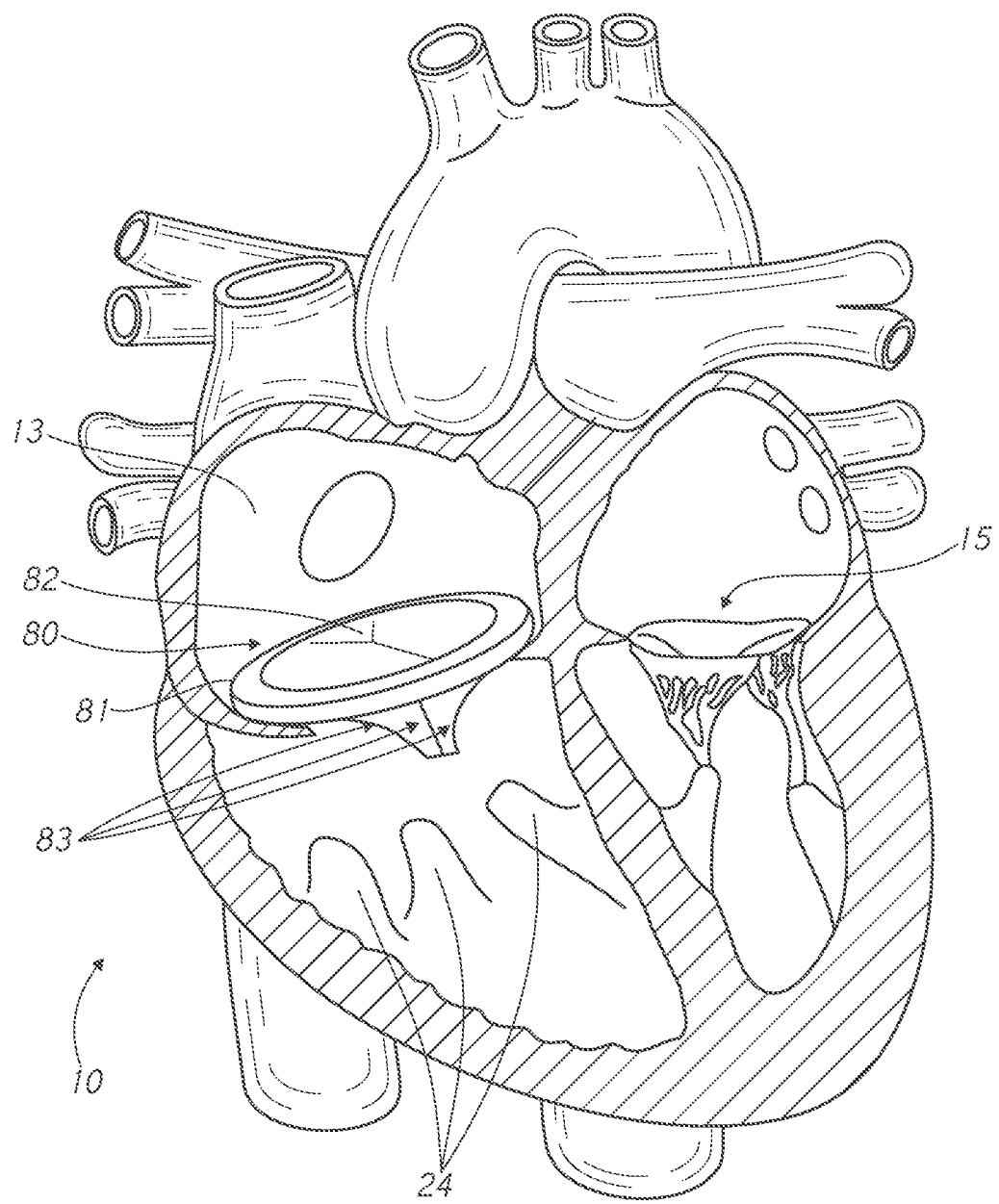
FIG. 7 is a cross-sectional view of a heart with a prosthetic valve assembly implanted in place of the native tricuspid valve in accordance with one or more embodiments.
Figure 8:
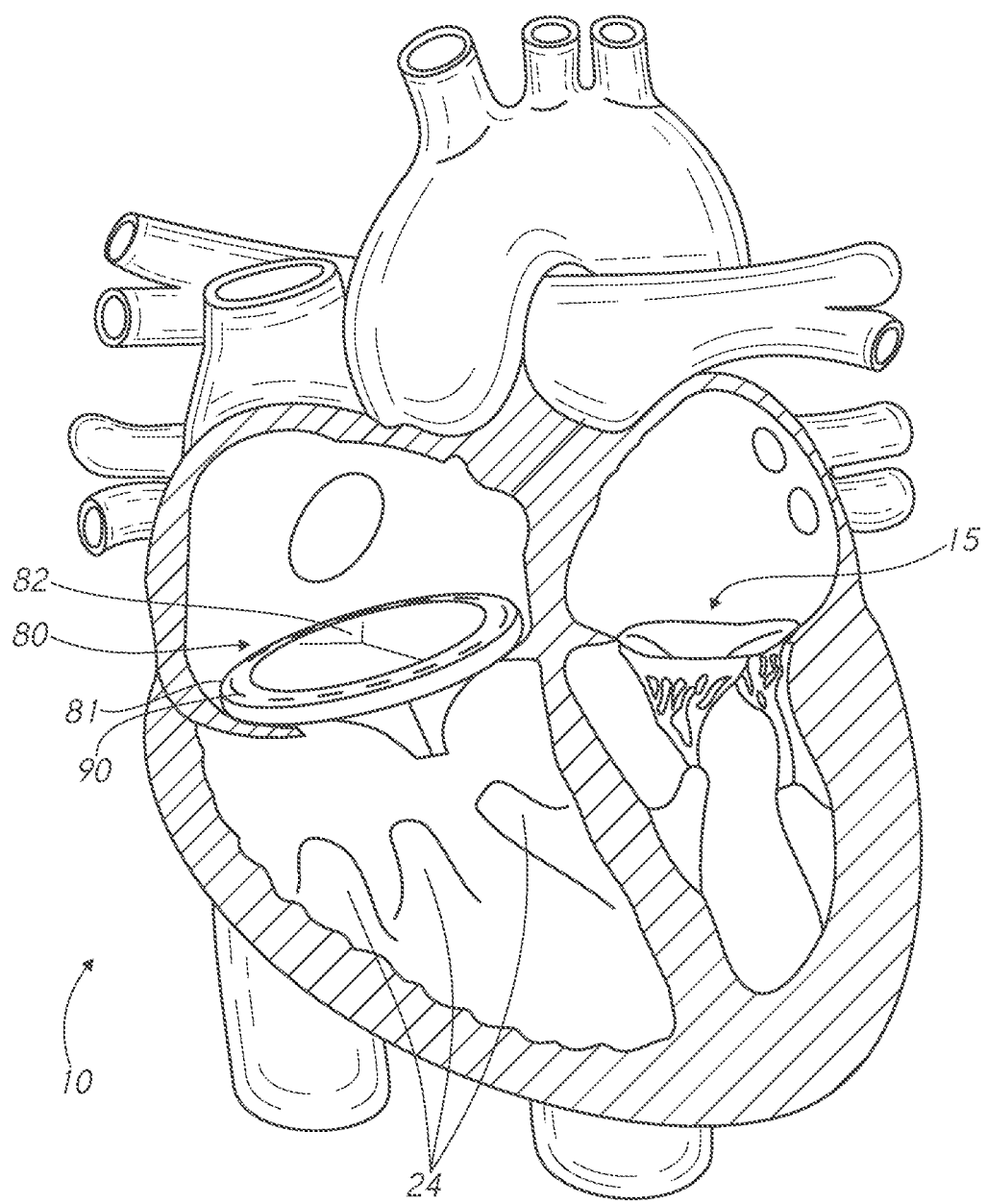
FIG. 8 is a cross-sectional view of a heart with a prosthetic valve assembly implanted in place of the native tricuspid valve in accordance with one or more embodiments, wherein the prosthetic valve assembly is sutured to the native heart tissue.

In certain embodiments, a prosthetic valve assembly is surgically implanted to fill in the resulting tricuspid valve gap 70. A particular embodiment of a prosthetic valve assembly 80 is shown in FIG. 7, comprising an annuloplasty ring 81 attached to a prosthetic valve 82 having prosthetic valve leaflets 83. In certain embodiments, the prosthetic valve assembly 80 includes a prosthetic valve 82 with three prosthetic leaflets 83, matching the number of the native leaflets in a typical native tricuspid valve 20, which the valve assembly 80 may effectively replace. In one exemplary embodiment, the size, positioning, shape, and/or other physical characteristics of the prosthetic valve leaflets 83 substantially match or approximate the corresponding physical properties of the removed, native heart valve leaflets. Imaging techniques can be used to measure the shape(s) and/or size(s) of the native annulus and/or leaflets, and the size(s) and/or shape(s) of the prosthetic valve assembly and/or its components may be selected based at least in part on the measured values.

The placement of the prosthetic valve assembly can be at least partially above and/or below the dividing wall between the right atrium 13 and the right ventricle 14, or anywhere where the prosthetic valve assembly may advantageously appropriately allow flow of blood from the right atrium 13 and into the right ventricle 14 substantially without backflow. In certain embodiments, the prosthetic tricuspid valve assembly 80 is secured at least in part to the native heart tissue in an analogous fashion to the disclosed embodiments relating to the attachment of the prosthetic mitral valve assembly 40 described above and shown in FIGS. 3-5. In some embodiments, the prosthetic tricuspid valve assembly 80 can be secured to the native tissue of the heart without removing the native tricuspid valve 20, or only partially removing the native tricuspid valve.

A prosthetic valve assembly can be at least partially secured in some manner to the native heart tissue. In the embodiment shown in FIG. 8, the annuloplasty ring 81 of the prosthetic valve assembly 80 is sutured 90 or otherwise connected to the heart tissue, such as to a portion of the dividing wall between the right atrium 13 and right ventricle 14, such that blood flows through the prosthetic valve 82 from the right atrium 13 into the right ventricle 14, but not backward to a substantial degree when the heart is functioning. In the embodiment shown, the annuloplasty ring 81 of the prosthetic valve assembly 80 is placed above and resting on the divide between right atrium 13 and right ventricle 14. In some embodiments, the prosthetic valve assembly 80 can be secured to native heart tissue other than the dividing wall between the atrium and ventricle and/or can be secured via different means (e.g., hooks, pledgets, pressure/friction fitting, metal, plastic, composite or other clips, metal mesh, etc.) to the same or different structures on the prosthetic valve assembly 80 than the annuloplasty ring 81 (e.g., the prosthetic valve or prosthetic valve leaflets). For a pressure fit, the outward radial pressure of the prosthetic valve assembly 80 and/or annuloplasty ring 81 against the surrounding tissue can assist at least in part in retaining the valve assembly in place.

Figure 9:
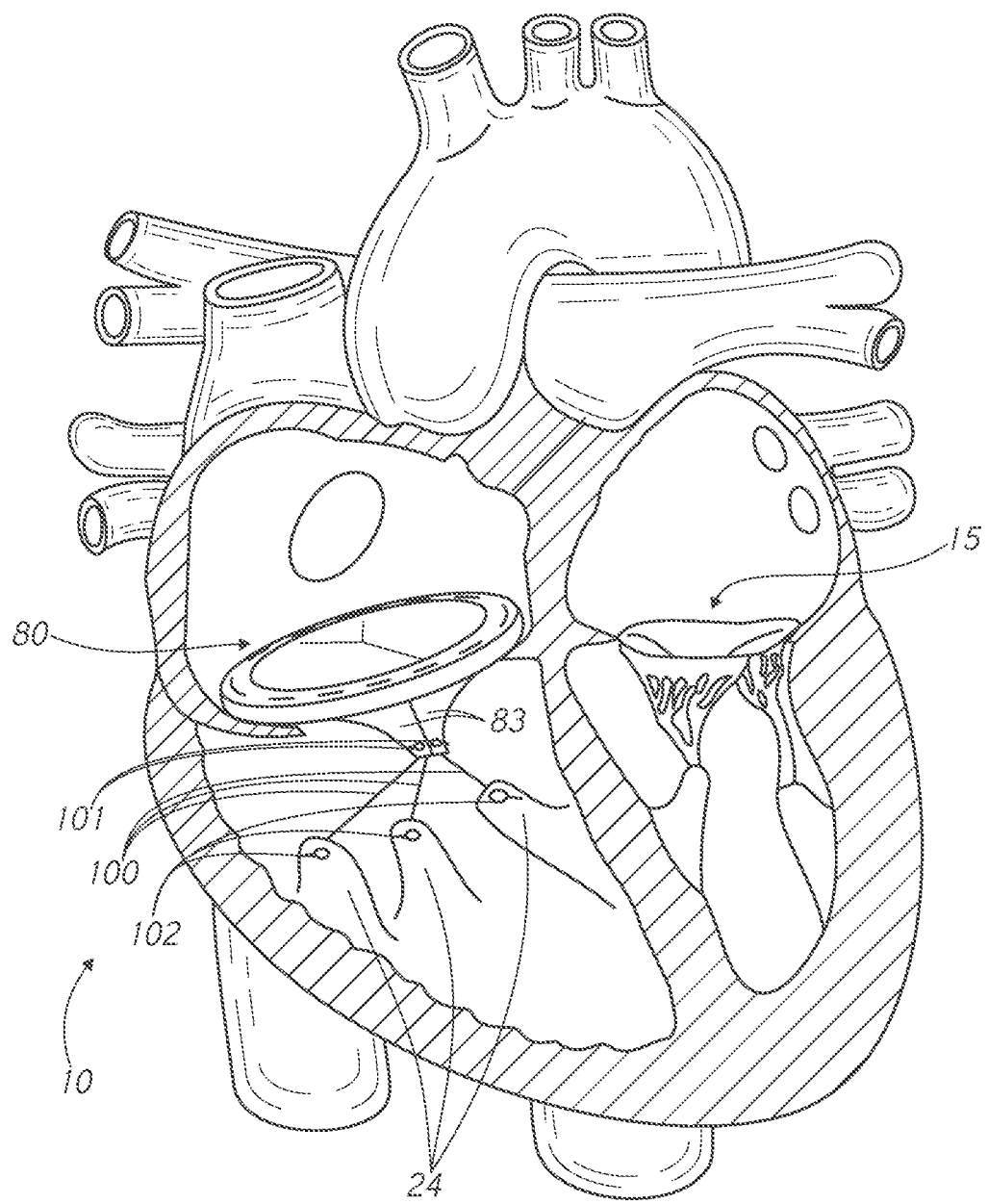
FIG. 9 is a cross-sectional view of a heart with an embodiment of a prosthetic valve assembly implanted in place of a native tricuspid valve in accordance with one or more embodiments, wherein the leaflets of the prosthetic valve assembly are coupled to the native papillary muscles of the right ventricle by tensioning members to simulate chordae tendineae.

In certain embodiments, one or more prosthetic valve leaflets 83 are anchored to native heart tissue. As shown in FIG. 9, the prosthetic valve leaflet(s) 83 can be anchored in some manner to native papillary muscles 24. FIG. 9 shows one embodiment wherein the prosthetic valve assembly 80 mimics the structure of the native tricuspid valve 20, having three leaflets 83 (two shown in FIG. 9). Each prosthetic leaflet 83 can accordingly be anchored to an existing, native papillary muscle 24. In the particular embodiment shown in FIG. 9, prosthetic leaflets 83 are tethered or otherwise coupled to the native papillary muscles 24 via tethers 100, prosthetic valve leaflet anchors 101 and papillary muscle anchors 102, though other methods can also be used to anchor the prosthetic leaflets to the native tissue of the heart. Alternatively, the prosthetic valve leaflets 83 could be anchored to native heart tissue anywhere in or through the right ventricle 14 or surrounding tissue.

In some implementations, the present disclosure provides methods for replacing a native cardiac valve with a prosthetic valve assembly in accordance with aspects of the various embodiments disclosed herein. Such methods may include multiple procedures occurring on different days, or at different times. In some embodiments, removal of the native cardiac valve and/or placement and attachment of a prosthetic valve assembly in the native valve's place occurs in connection with a first procedure, while attachment of prosthetic leaflets of the prosthetic valve to native heart tissue may occur in connection with a second procedure on a later day, or at a later time. Such a two-procedure format may allow patients and surgeons more procedural flexibility and can make more valve replacements viable for patients who are less likely to be able to endure the stresses of longer surgeries. Said first procedure may also not include removal of the native cardiac valve in some implementations.

FIGS. 10A-10F show example stages of one or more embodiments of a procedure for anchoring prosthetic valve leaflets of a prosthetic valve assembly to native heart tissue. The illustrated anchoring procedures can be applied in, or relevant to, any of the various embodiments disclosed herein. Further, methods of attachment and anchoring of the prosthetic valve leaflets other than those shown in FIGS. 10A-10F can be used. In the embodiment shown in FIG. 10A, a shafted instrument 111 may be advanced through the apex of the heart 110, or other portion of the heart 110, for example, near the apex. A needle, either inside the shafted instrument 111 or integrated with the end of the shafted instrument 111, may be advanced through a prosthetic valve leaflet (e.g., leaflet 43a). The needle may be at least partially withdrawn, thereby deploying an anchor (e.g., anchor 112a). For example, the anchor 112a can comprise a coated, and/or coiled guide wire having a suture woven therethrough. The suture may advantageously be made at least in part of polytetrafluoroethylene (PTFE), or the like. When the suture is pulled, such action may at least partially cause the coiled guidewire to deform into a predetermined shape (e.g., a figure-eight or knot-like shape) above the leaflet. A figure-eight or knot-like structure including a suture and coiled guidewire may provide the prosthetic leaflet anchor 112a. In another embodiment, the anchor comprises a knot made from suture, for example, ePTFE suture that features a low-profile insertion configuration and a higher profile anchoring configuration. Embodiments of anchors and procedures for implanting anchors in accordance with aspects of the present disclosure are described in further detail in U.S. Patent Publication No. 2014/0114404, which is incorporated by reference in its entirety for all purposes. The anchor 112a can take a wide variety of different forms. For example, the anchor can comprise a pledget form or structure, any type of knot configuration, a metal or other rigid-type clip, a metal mesh, etc.

Figure 10A:
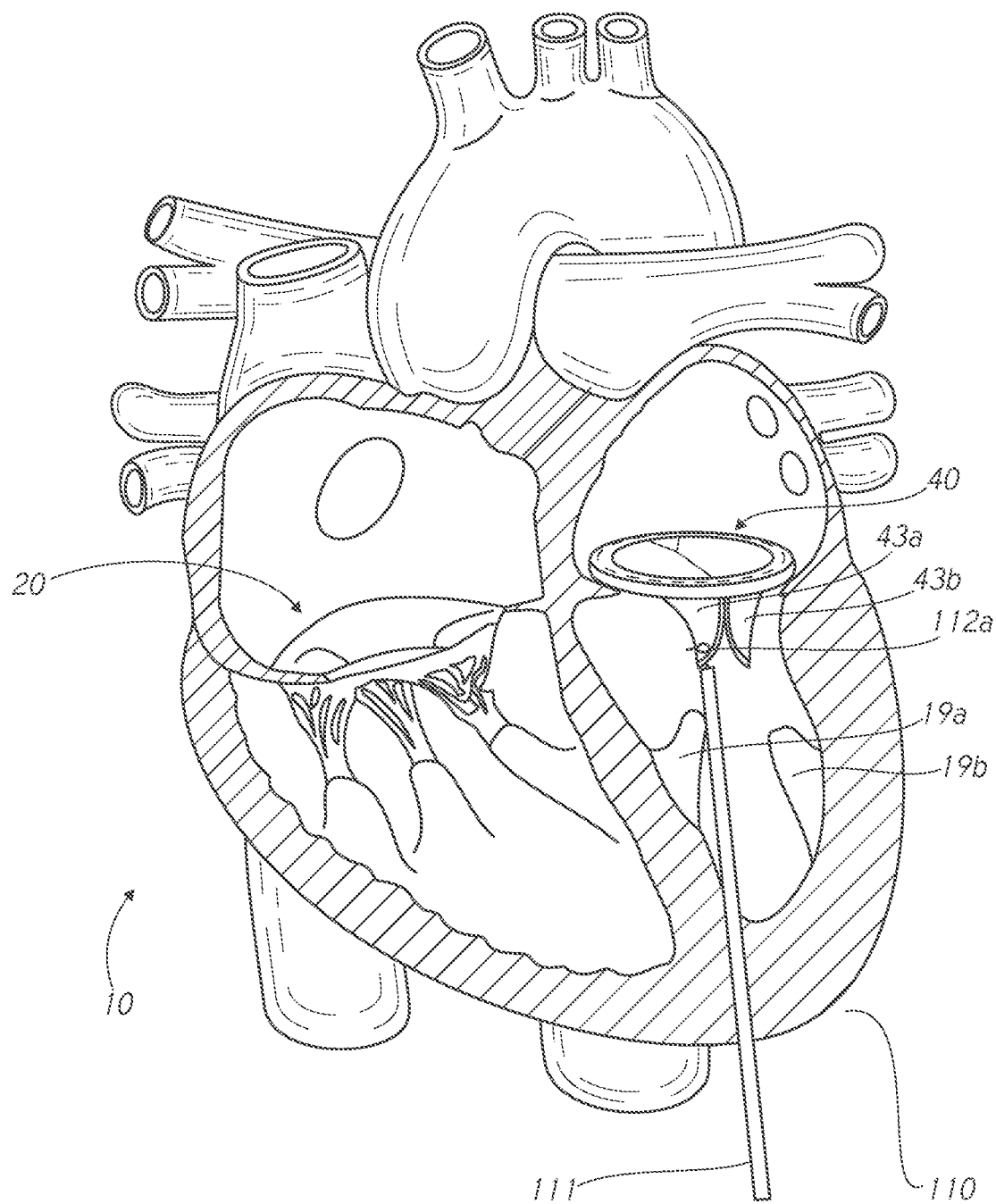
FIGS. 10A-10F are cross-sectional views of a heart showing a prosthetic valve assembly implanted in place of the native mitral valve and sutured to the native heart tissue in accordance with one or more embodiments, wherein the prosthetic valve leaflets are anchored to the native papillary muscles of the left atrium in a transapical procedure.
Figure 10B:
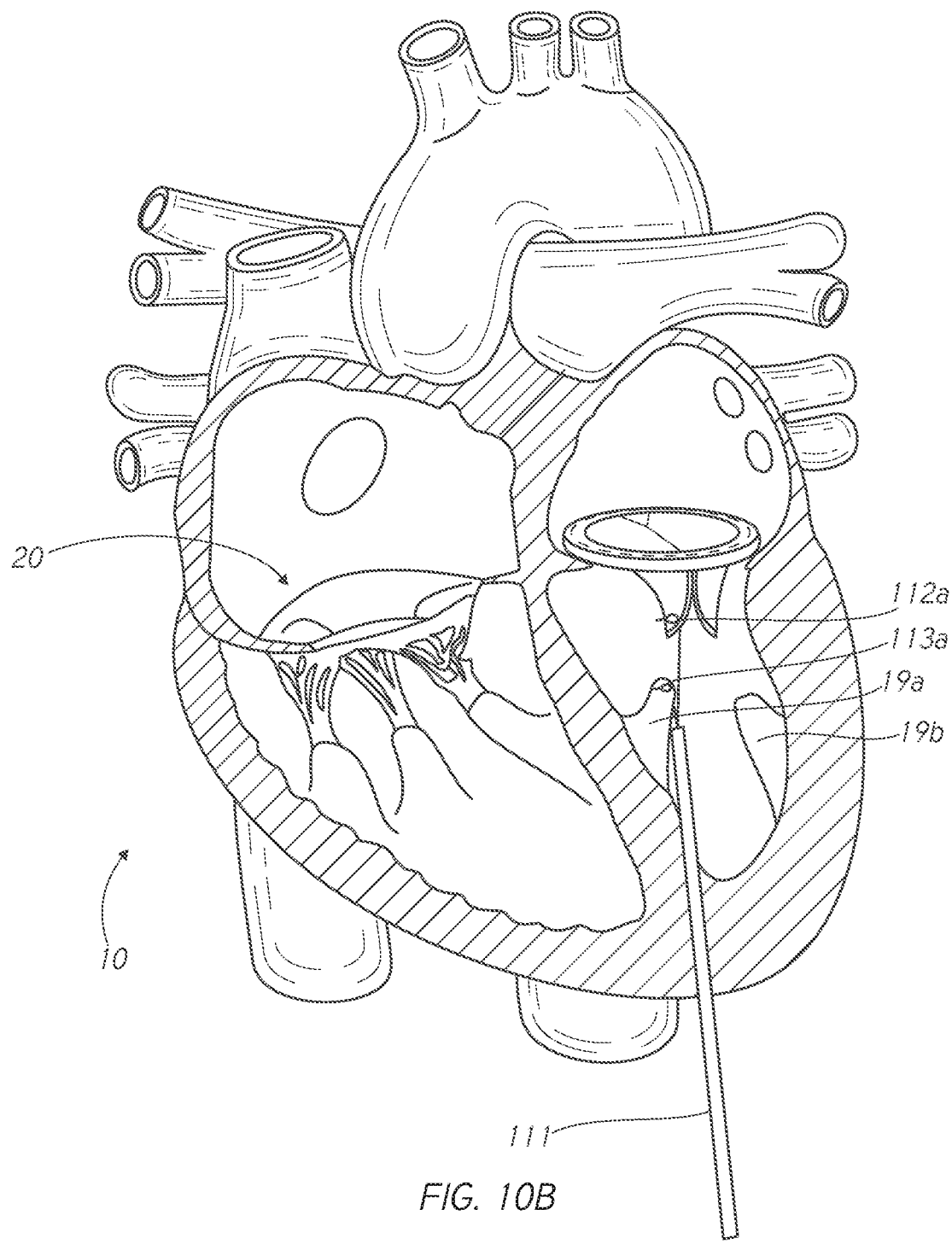
Figure 10C:
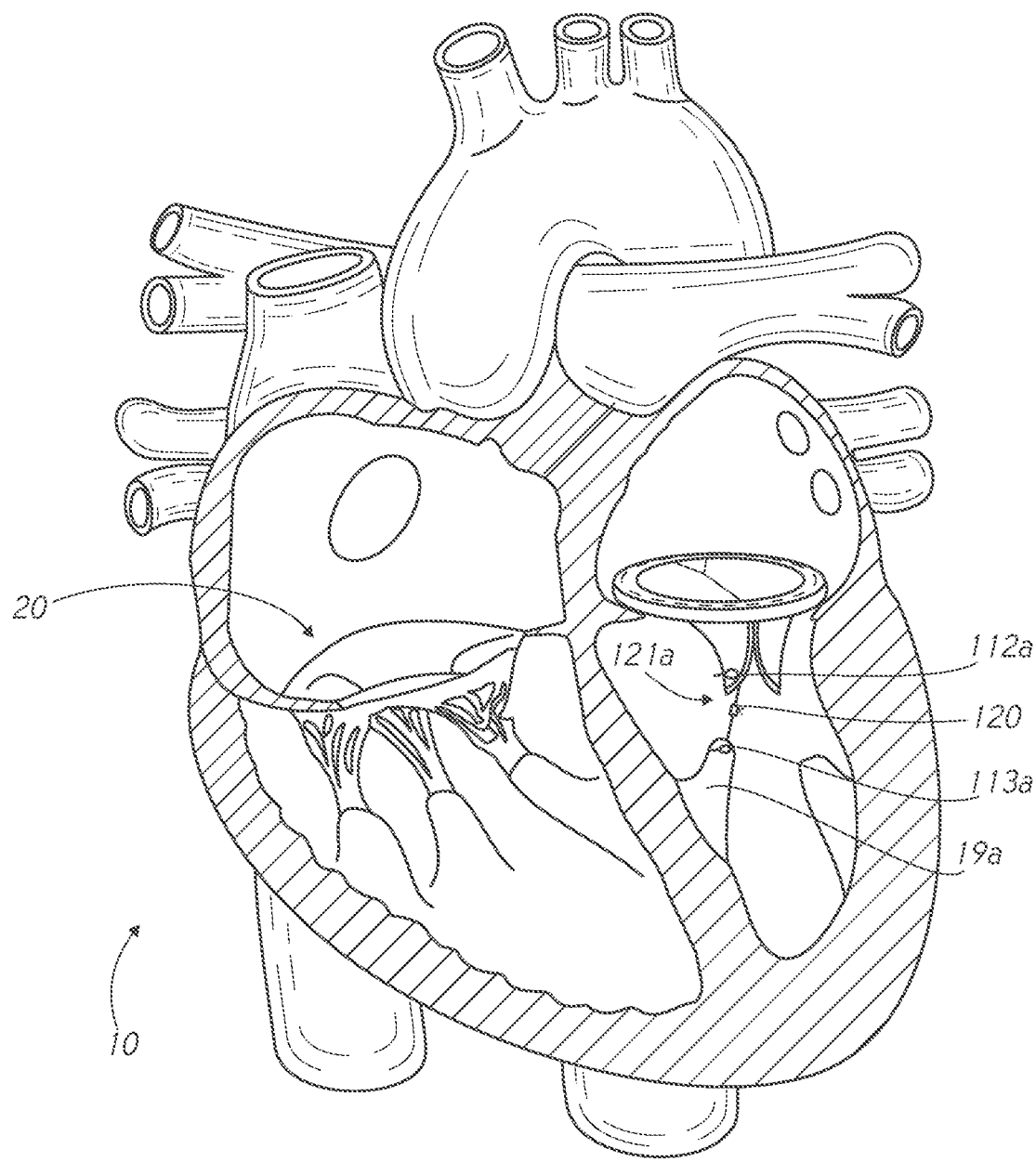

In the embodiment shown in FIG. 10B, the shafted instrument 111 may be retracted below a papillary muscle 19a, or otherwise drawn into proximity therewith, and a needle may be advanced at least partially through the papillary muscle 19a. In a similar fashion to the deployment of prosthetic leaflet anchor 112a, a papillary muscle anchor 113a may be deployed, such as by withdrawing the needle and pulling on a suture, thereby causing deformation of a coiled guidewire into a predetermined shape (e.g., a figure-eight or knot-like shape). As noted above, prosthetic valve leaflets can alternatively be anchored to other native tissue of the heart in addition to, or as an alternative to, papillary muscle(s), such as the corresponding ventricle wall, septal wall, or through the heart wall or surrounding tissue. Such anchoring may be accomplished using sutures, pledgets, hooks, clips, and/or other methods. Refer again to U.S. Patent Publication No. 2014/0114404 for one or more anchoring methods. Again, the anchor 112a can take a wide variety of different forms other than configuration(s) related to U.S. Patent Publication No. 2014/0114404.

In the embodiments shown in FIGS. 10A-10F, the sutures integrated into prosthetic leaflet anchor 112a and papillary muscle anchor 113a may be separate sutures. In order to couple such separate sutures, one or more coupling members 120, shown in FIG. 10C, may be used. Coupling member(s) 120 can comprise a clip, cinching member, knot, or any other suitable means of joining two sutures or components. In some embodiments, sutures integrated into prosthetic leaflet anchor 112a and/or papillary muscle anchor 113b can be the same suture. That is, different ends of the same suture may be integrated into separate prosthetic leaflet and papillary muscle anchors. The resulting prosthetic chordae 121a may be adjustable with respect to length at least in part by knotting, tying, cutting, anchoring, and/or otherwise manipulating in any way to achieve the desired or optimal length (e.g., the length at which the relevant prosthetic valve leaflet will coapt with its partners, but not prolapse).

Figure 10D:
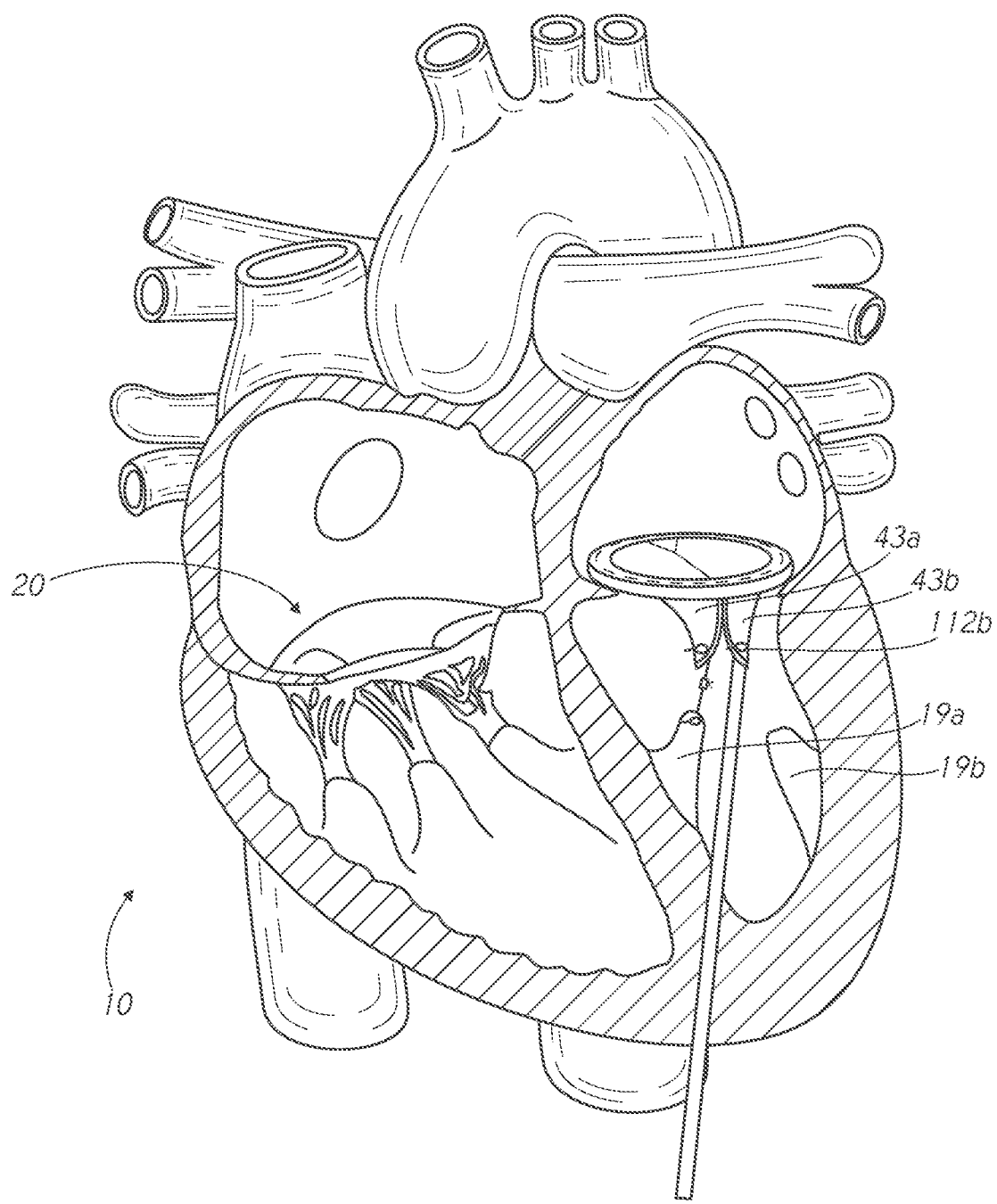
Figure 10E:
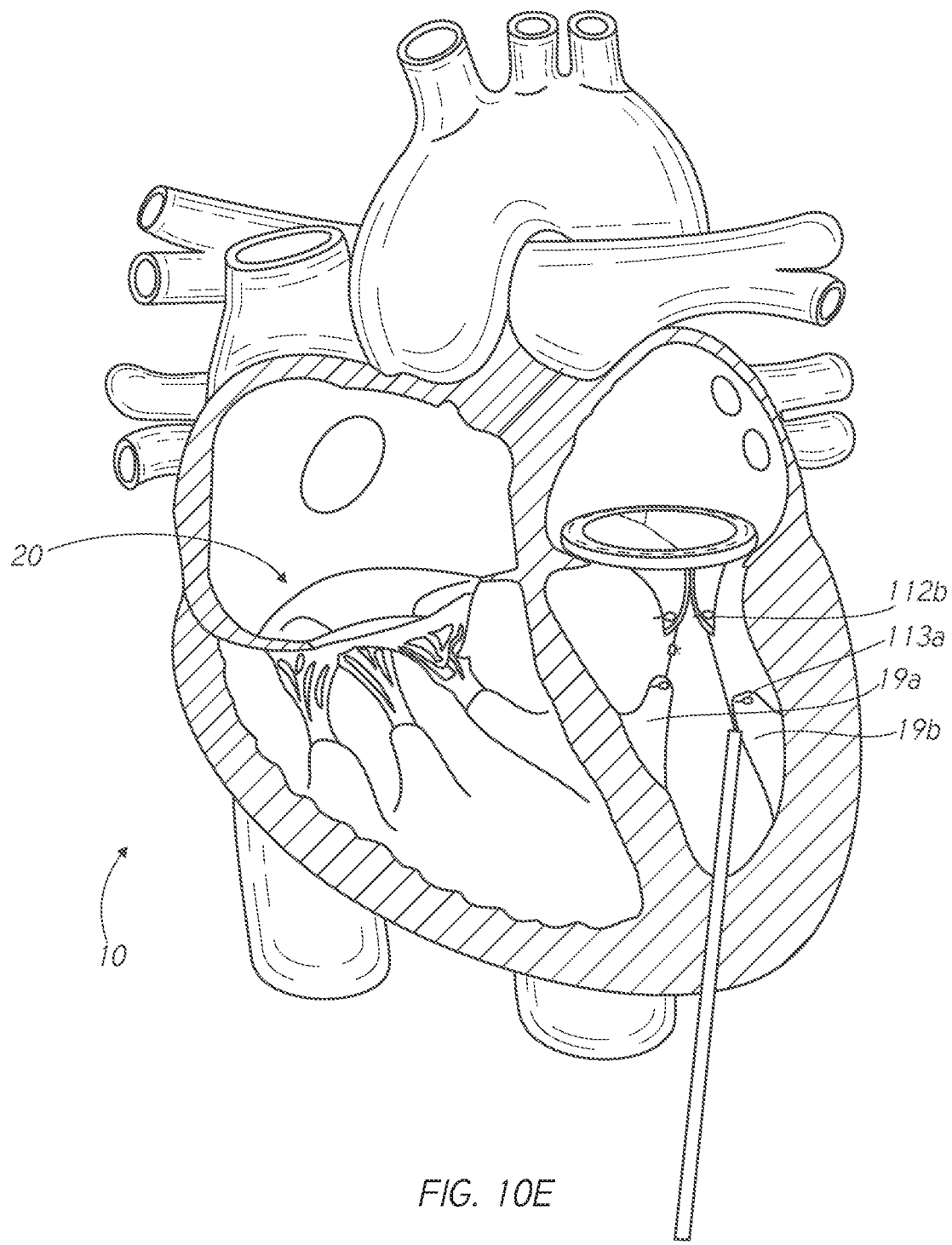
Figure 10F:
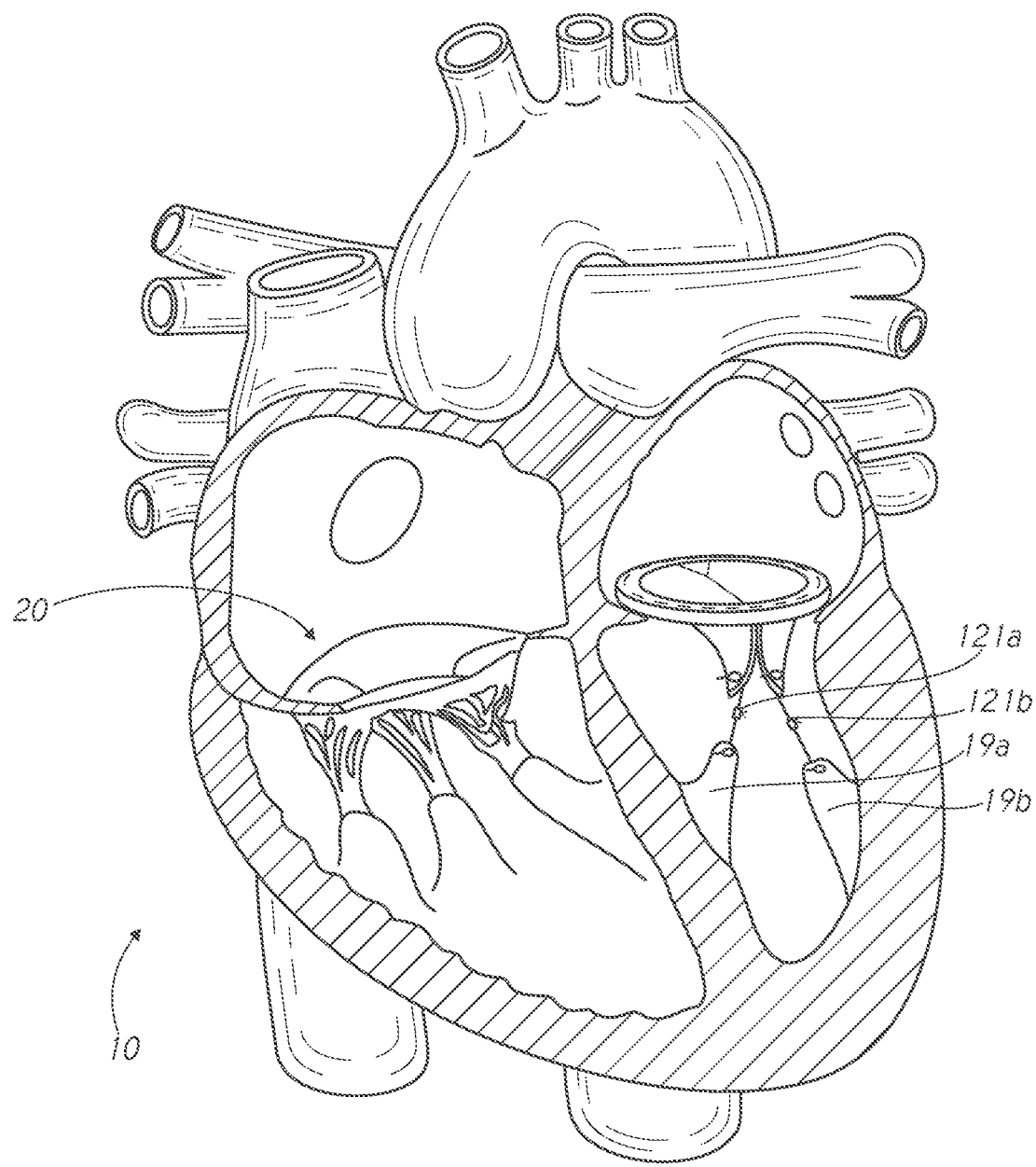

FIGS. 10D-10F show the anchoring of a second prosthetic valve leaflet 43b in a fashion similar to that in which prosthetic valve leaflet 43a is anchored, as described above. Although the prosthetic chordae 121a, 121b (see Figure F) are shown attached at the same relative vertical position or height on the respective prosthetic valve leaflets 43a, 43b, the prosthetic chordae 121a, 121b can be attached asymmetrically relative to each other in some embodiments. In other words, the prosthetic chordae 121a, 121b can be attached at different heights along the length of the prosthetic valve leaflets 43a, 43b. Additionally, the prosthetic chordae 121a, 121b can differ in length, such as in order to achieve asymmetrical coupling between the prosthetic leaflets 43a, 43b. Thus, prosthetic leaflets 43a and 43b may be anchored to native heart tissue, such as the papillary muscles 19a, 19b, which may at least partially prevent prolapse of prosthetic leaflets 43a and 43b, while also allowing the leaflets to properly coapt. Although only a single prosthetic chord for each leaflet is illustrated in FIG. 10F, some embodiments may include two or more chords secured to a single leaflet. Some examples can include a different number of prosthetic chordae secured to each leaflet. In certain embodiments, anchoring process(es) can be used analogously to anchor prosthetic leaflets of a prosthetic tricuspid valve assembly or other prosthetic cardiac valve assemblies to the native tissue of the heart.

FIGS. 11A-11C illustrate perspective views of different configurations of annuloplasty rings in accordance with one or more embodiments of the present disclosure.

Having illustrated and described the principles of the illustrated embodiments, it will be apparent that the embodiments can be modified in arrangement and detail without departing from such principles.

Further, although the prosthetic valve assemblies of this disclosure are shown generally circular in cross section, these prosthetic valve assemblies can have a D-shape, an oval shape or any other shape suitable for fitting the contours of the relevant, replaced, native mitral valve or native tricuspid valve. Furthermore, the prosthetic valve assembly can be coated to reduce the likelihood thrombus formation and/or to encourage tissue ingrowth using coatings or coverings known in the art.

In view of the many possible embodiments, it will be recognized that the illustrated embodiments include only examples and should not be taken as a limitation on the scope of the disclosure. Rather, the scope is defined only by the following claims. We therefore claim all such embodiments that come within the scope of these claims.

I claim:

1. A method of replacing a native heart valve, the method comprising:
   in a first surgical procedure:
      providing open-chest access to a heart of a patient;
      surgically removing at least a portion of a native heart valve of the heart; and
      attaching a prosthetic valve assembly comprising prosthetic valve leaflets in place of the native heart valve; and
   in a second transcatheter procedure:
      anchoring the prosthetic valve leaflets to native papillary muscles of the heart at least in part by attaching a chord associated with each of the prosthetic valve leaflets to a respective one of the native papillary muscles.

2. The method of claim 1, further comprising:
   during the first surgical procedure, placing an annuloplasty ring component of the prosthetic valve assembly in a left atrium of the heart; and
   during the second transcatheter procedure, suturing the annuloplasty ring component to an annulus of the native heart valve from within a left ventricle of the heart.

3. The method of claim 1, wherein the first surgical procedure and the second transcatheter procedure are performed on separate days.

4. The method of claim 1, wherein said anchoring the prosthetic valve leaflets to the native papillary muscles of the heart comprises:
   securing a first suture to a first papillary muscle; and
   coupling the first suture to a second suture secured to one of the prosthetic valve leaflets using a coupling member.

5. The method of claim 4, wherein the coupling member comprises a clip.

6. The method of claim 4, wherein the coupling member comprises a cinching member.

7. The method of claim 4, wherein the coupling member comprises a knot.

8. The method of claim 1, wherein the native heart valve is a mitral valve.

9. The method of claim 1, wherein the native heart valve is a tricuspid valve.

10. The method of claim 1, during the second transcatheter procedure, suturing a portion of the prosthetic valve assembly to cardiac tissue.

11. The method of claim 10, wherein the cardiac tissue is disposed in a left atrium of the heart.

12. The method of claim 10, wherein the cardiac tissue is disposed in a left ventricle of the heart.

13. The method of claim 1, wherein the second transcatheter procedure is a transapical procedure.

14. The method of claim 1, wherein the prosthetic valve assembly comprises, an annuloplasty ring, the prosthetic valve leaflets being directly coupled to the annuloplasty ring.

15. The method of claim 14, wherein the prosthetic valve leaflets are sutured to the annuloplasty ring.

16. The method of claim 1, wherein said attaching the prosthetic valve assembly in place of the native heart valve involves placing a ring portion of the prosthetic valve assembly above a divide between a left atrium and a left ventricle of the heart.

17. The method of claim 1, wherein said attaching the prosthetic valve assembly in place of the native heart valve involves placing a ring portion of the prosthetic valve assembly below a divide between a left atrium and a left ventricle of the heart.

* * * * *